(12) United States Patent
Swami et al.

(10) Patent No.: US 9,872,881 B2
(45) Date of Patent: Jan. 23, 2018

(54) BONE AND METAL TARGETED POLYMERIC NANOPARTICLES

(71) Applicants: The Brigham and Women's Hospital, Inc., Boston, MA (US); Massachusetts Institute of Technology, Cambridge, MA (US)

(72) Inventors: Archana Swami, Boston, MA (US); Pamela Basto, Cambridge, MA (US); Jeffrey Karp, Brookline, MA (US); Omid C. Farokhzad, Waban, MA (US)

(73) Assignees: The Brigham and Women's Hospital, Inc., Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/531,466

(22) Filed: Nov. 3, 2014

(65) Prior Publication Data

US 2015/0125391 A1 May 7, 2015

Related U.S. Application Data

(60) Provisional application No. 61/899,089, filed on Nov. 1, 2013.

(51) Int. Cl.
*A61K 9/00* (2006.01)
*A61K 38/05* (2006.01)
(Continued)

(52) U.S. Cl.
CPC .......... *A61K 38/05* (2013.01); *A61K 38/1875* (2013.01); *A61K 47/48084* (2013.01);
(Continued)

(58) Field of Classification Search
CPC ...................................................... A61K 38/05
See application file for complete search history.

(56) References Cited

U.S. PATENT DOCUMENTS

| 8,952,131 B2* | 2/2015 | Berasi | C07K 14/51 435/69.1 |
| 2011/0245528 A1* | 10/2011 | Schwartz | A61K 49/0002 560/60 |
| 2012/0070503 A1* | 3/2012 | Dixon | A61K 31/5415 424/497 |

OTHER PUBLICATIONS

Swami, Engineered nanomedicine for myeloma and bone microenvironment targeting, PNAS, 2014, 111, 10283-10292.*

(Continued)

*Primary Examiner* — Paul Dickinson
(74) *Attorney, Agent, or Firm* — Pabst Patent Group LLP

(57) ABSTRACT

Bone- and metal-targeted polymeric nanoparticles are provided. Exemplary nanoparticles have three main components: 1) a targeting element that can selectively bind to bone, minerals, or metal ions; 2) a layer of stealth to allow the polymer to evade immune response; and 3) a biodegradable polymeric material, forming an inner core which can carry therapeutics or other diagnostics. Preferred nanoparticles contain a blend of target-element polymer conjugate and polymer that optimizes the ligand density on the surface of the nanoparticle to provide improved targeting of the nanoparticle. The ratio of target-element polymer conjugate to polymer can also be optimized to improve the half-life of the nanoparticles in the blood of the subject. The nanoparticles also exhibit prolonged, sustained release of therapeutic agents loaded into the particles.

21 Claims, 14 Drawing Sheets

(51) Int. Cl.
A61K 38/18 (2006.01)
A61K 47/48 (2006.01)
(52) U.S. Cl.
CPC .. *A61K 47/48907* (2013.01); *A61K 47/48915* (2013.01); *A61K 47/48992* (2013.01)

(56) References Cited

OTHER PUBLICATIONS

Benyettou, et al., "PEGylated Versus Non-PEGylated $^3$Fe2O3@Alendronate Nanoparticles", J Bioanal Biomed., 4(3 (2012).
Choi and Kim, "Design of surface-modified poly(D,L-lactide-co-glycolide) nanoparticles for targeted drug delivery to bone", J Controlled Rel., 122:24-30 (2007).
Clementi, et al., "Dendritic poly(ethylene glycol) bearing paclitaxel and alendronate for targeting bone neoplasms", Mol Pharmaceutics, 8:1063-72 (2011).
Fishbein, et al., "Bisphosphonate-mediated gene vector delivery from the metal surfaces of stents", PNAS, 103(1):159-64 (2006).
Ozcan, et al., "Synthesis and characterization of surface-modified PBLG nanoparticles for bone targeting: in vitro and in vivo evaluations", J Pharmaceutical Sci., 100(11):4877-87 (2011).
Pan, et al., "Biodistribution and pharmacokinetic studies of bone-targeting N-(2-hydroxypropyl)methacrylamide copolymer-alendronate conjugates", Mol. Pharmaceutics, 5(4):548-58 (2008).
Thamake, et al., "Alendronate coated poly-lactic-co-glycolic acid (PLGA) nanoparticles for active targeting of metastatic breast cancer", Biomaterials, 33 (29):7164-73 (2012).
Van Alsten, "Self-assembled monolayers on engineering metals: structure, derivatization, and utility", Langmuir, 15:7605-14 (1999).
Wang, et al., "Bisphosphonate-coated BSA nanoparticles lack bone targeting after systemic administration", J Drug Targeting, 18(8):611-26 (2010).

* cited by examiner

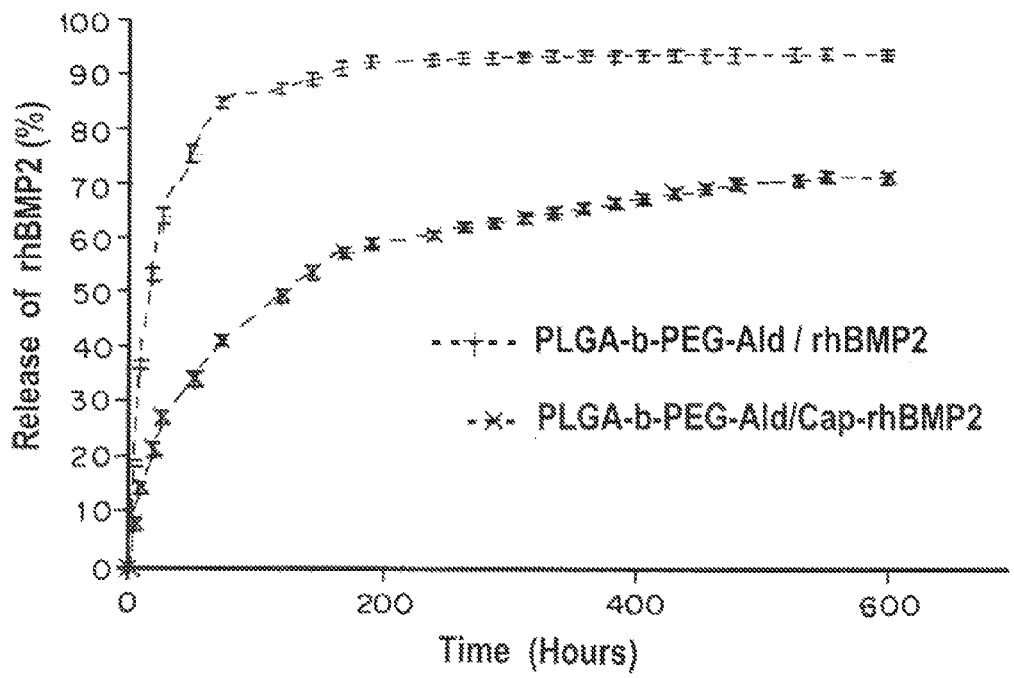
FIG. 5A
FIG. 5B
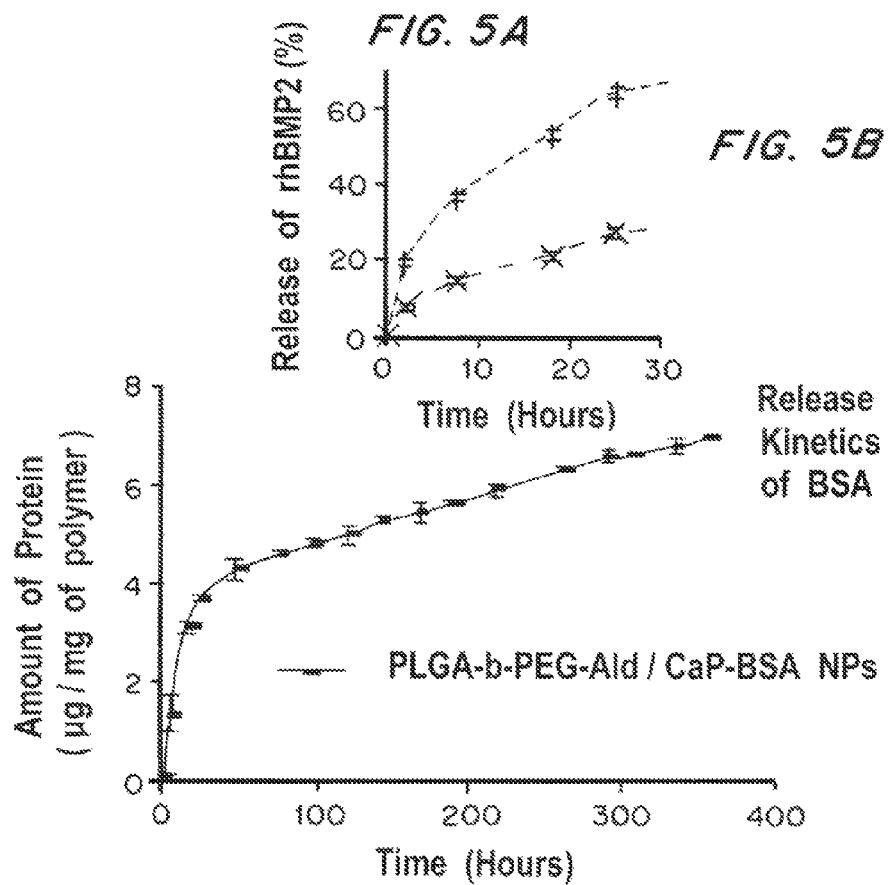
FIG. 6A

— ♦ — Cells (Free rhBMP2, Day 1)  — ■ — PLGA-b-PEG-Ald
— ▲ — PLGA-b-PEG-Ald / CaP  — ✕ — PLGA-b-PEG-Ald / rhBMP2
— ● — PLGA-b-PEG-Ald / CaP-rhBMP2

— ♦ — Cells (Free rhBMP2, Day 1)   — ■ — PLGA-b-PEG-Ald
— ▲ — PLGA-b-PEG-Ald / CaP   — ✕ — PLGA-b-PEG-Ald / rhBMP2
— ● — PLGA-b-PEG-Ald / CaP-rhBMP2

NPs labeled with PLGA-Alexa647 in Femur and Spine of mice Quantified from Histology. (Time point: 24h after injection)

BONE AND METAL TARGETED POLYMERIC NANOPARTICLES

CROSS-REFERENCE TO RELATED APPLICATIONS

This application claims the benefit of priority to U.S. Ser. No. 61/899,089, filed on Nov. 1, 2013, the disclosure of which is incorporated herein by reference.

FIELD OF THE INVENTION

This invention is generally directed to the field of nanoparticles including nanoparticles for drug delivery.

BACKGROUND OF THE INVENTION

Three-fourths of the patients with breast and prostate cancer develop complications of bone metastasis. When cancer metastasizes to bone, it becomes almost incurable and creates considerable pain. Metastasizing cancer also deregulates bone remodeling, leading to bone fractures, hypercalcaemia, spinal cord and nerve compression syndromes.

The mineralized extracellular matrix and specific cell types in the bone microenvironment are controlled by local and systemic factors that create a special milieu to provide a fertile soil for many cancers in which to thrive, including metastasizing cancer from other distant organs and areas of the body. Cancer cells in bone secrete a vast array of proteins, many of which interact with resident cells in the bone marrow to induce the differentiation, recruitment and activation of osteoclasts and osteoblasts, inducing destructive osteolytic and/or bone forming osteoblastic lesions.

During the process of bone resorption, stored growth factors and ionized calcium are released from the mineralized bone matrix. These factors feedback to promote tumor cell growth and production of osteolytic and osteoblastic factors. This vicious cycle can support tumor growth in bone. The fertile environment of bone marrow can also serve as a storage space for dormant cancer cells, as these cancer cells can significantly resist localized radiation treatment and systemic chemotherapeutic attack, and later emerge as full-blown metastases in bone or other organs. Preferential delivery of therapeutic agents to the bone has potential to attach to these bone homing cancer cells and may significantly improve the clinical outcome.

There are several other bone disorders that would benefit from systems that can deliver therapeutics preferentially to bone. The common bone disorders such as osteoporosis, Paget's disease, multiple myeloma, myelo-proliferative disease besides skeletal metastasis of several epithelial cancers can have better treatment options if the therapeutic agents could be delivered in a site specific manner to bone.

In the case of designing and development of surgical implants used for applications such as joining of bones, research has been focused only on topological modification of implant surfaces for better integration of the implant into the tissue. Some preclinical studies have suggested coating of the implant surface with polymers or entrapping therapeutic molecules on the implant may have benefits. However, these strategies are limited by the harsh conditions and time-consuming procedures for coating the device, and offer little for practical applications.

There has been literally no practical solution when it comes to intraoperative modification procedure of the surgical implants for local drug delivery of therapeutics such as antibiotics, growth factors etc., for individualized patient treatment. There is a complete absence of any method that can provide flexibility of modifying surgical implants during an operation or in emergencies. A specific method or composition is needed for delivery of therapeutic molecules such as growth factors like bone morphogenic protein that can have drastic side effects on non-specific application and have short half-life, for example five minutes. Growth factors need to be at the site of implantation for days for effective bone formation at the implant surface. There is no effective strategy for local drug delivery at the surgical metal implant-bone tissue interface that can enhance osseointegration of implants in the tissue or that can actively promote the tissue growth at the implant surface.

It is therefore an object of the present invention to provide methods and compositions for targeting delivery of therapeutics for selective treatment of bone disorders.

It is another object of the present invention to provide methods and compositions for improving delivery of therapeutics at the tissue-implant interface.

SUMMARY OF THE INVENTION

Bone and metal-targeted polymeric nanoparticles have three main components: 1) a targeting element that selectively binds to bone, minerals, and/or metal ions; 2) a "stealth layer" to allow the nanoparticles to evade cell mediated immune response, including uptake by the reticuloendothelial system (the "RES"); and 3) a biodegradable polymeric material forming an inner core, which can carry therapeutic, prophylactic, or diagnostic agents. Preferred nanoparticles contain a blend of targeting element-amphiphilic polymer conjugate and amphiphilic polymer that optimizes the ligand density on the surface of the nanoparticle to provide improved targeting of the nanoparticle. The ratio of targeting element-polymer conjugate to polymer can also be optimized to improve the half-life of the nanoparticles in the blood of the subject. The nanoparticles exhibit prolonged, sustained release of therapeutic agents loaded into the particles.

An exemplary nanoparticle contains a tri-block co-polymer (e.g., BP-PEG-PLGA), blended with di-block copolymer (e.g., PEG-PLGA) to vary the PEG and targeting ligand density on nanoparticle surface, to maximum affinity to the bone mineral or metal surface, and minimize inflammatory response. Ratios of the targeting element-polymer conjugate (tri-block co-polymer, preferably targeting element-PEG-PLGA) to the polymer (di-block copolymer, preferably PEG-PLGA) are typically between 1:9 to 3:2, and preferably is 1:4 for bone targeting and 1:2 for metal targeting. The targeting component is typically a phosphonate.

The targeted nanoparticles are useful for targeted delivery of therapeutic agents, promoting osseointegration of implants, and delivering therapeutics to the bone for the treatment of bone disorders.

One embodiment provides a method of modifying surgical implants by coating the implant with metal targeted nanoparticles. The nanoparticles can be loaded with therapeutic agents for local delivery of the therapeutics at the tissue-metal surface interface at the site of implantation. The nanoparticles can locally deliver drugs for healing of bone wounds, non-union fractures, and spinal fusions, for increasing the rate of osseointegration and for decreasing infection. Bisphosphonate-conjugated nanoparticles stick effectively to metal implants (titanium based), allowing surgeons to modify the surface of surgical implants under intraoperative conditions, in a quick dip fashion, where the local and controlled delivery of drug at the implant-tissue interface in the surgical site can enhance osseous integration of the implant in the tissue.

BRIEF DESCRIPTION OF THE DRAWINGS

FIGS. 5A and 5B are line graphs of release of rhBMP2(%) versus time (hours) for PLGA-b-PEG-Ald/CaP-rhBMP2 (⁕) and PLGA-b-PEG-Ald/rhBMP2 (+).

FIG. 6A is a line graph of amount of bovine serum albumin (µg/mg of polymer) released versus time (hours) for PLGA-b-PEG-Ald/CaP-BSA NPs.

DETAILED DESCRIPTION OF THE INVENTION

I. Definitions

Figure 1A:
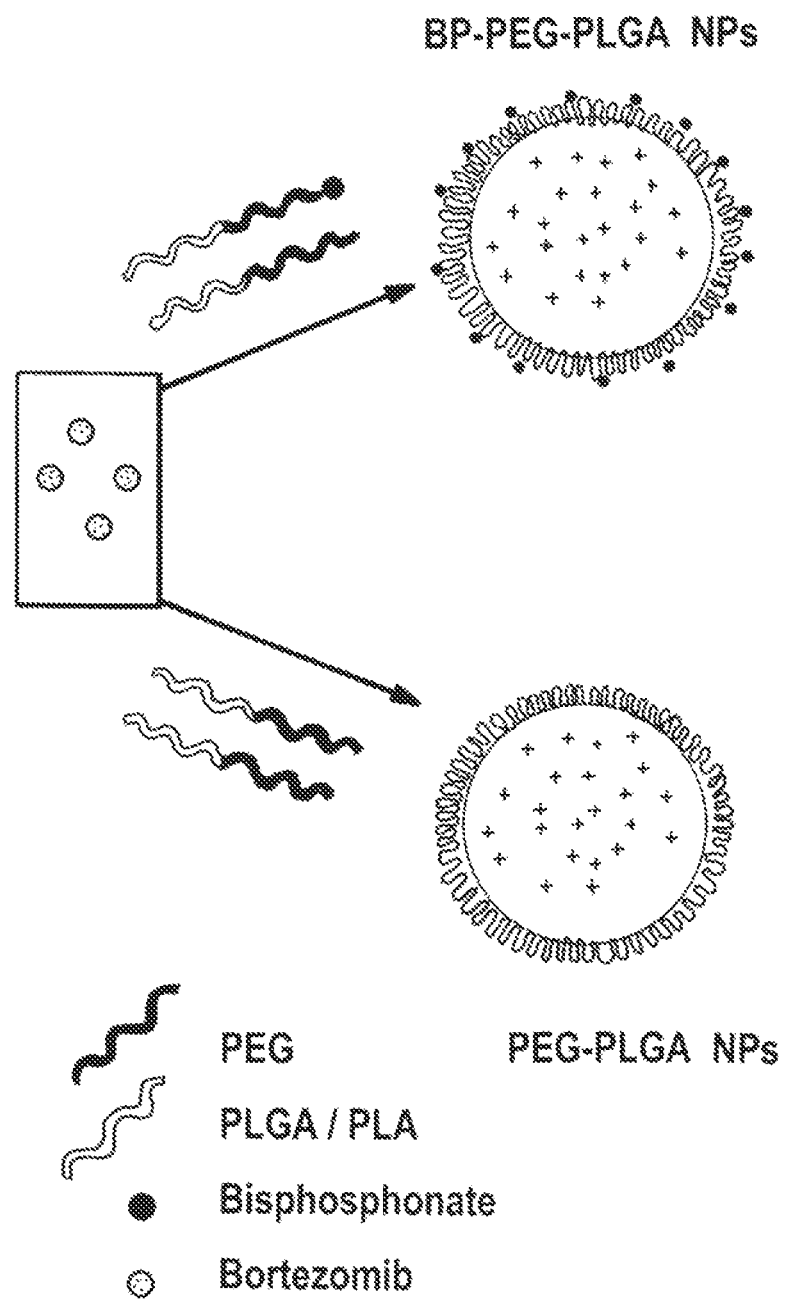
FIG. 1A is a schematic of a representative bone/metal targeted nanoparticle. Circles on the outside of the nanoparticle represent the targeting moiety, for example bisphosphonate.

The terms "treating" or "preventing", as used herein, can include preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

The term "bone", as used herein, refers to the mineralized rigid organs such as those forming all or part of the endoskeleton of a mammal, preferably a human. The bone can be any bone including the bones of the skull, pelvis, ribs, sternum, vertebra, the upper and lower limbs, the pectoral girdle, or the pelvic girdle. The bones can be the long bones such as the tibia, Tibia, femur, humerus, radius, or phalanges. Bone, as used herein, can refer to the osseous tissue, bone marrow, endosteum, periosteum, or cartilage. Bone can refer to natural or to non-natural, synthetic or semi-synthetic, bone products such as whole bones, sections of whole bone, bone chips, bone powder, bone tissue biopsy, collagen preparations, or mixtures thereof.

The terms "osseointegration" and "osteointegration", as used interchangeably herein, refer to the formation of a direct structural connection between living bone and the surface of an implant. The term "osseointegration" is often used in the dental field and "osteointegration" is used in reference to spinal/long bones as well as in reference to integration of replacement joints (such as, for example, hip, knee, shoulder, spine). Both terms refer to the integration of the implant into the surrounding bone tissue. The level of osseointegration of an implant can be determined by one of several methods. For example, the bone mineral density around an implant site, the area of bone/implant contact, bone volume, the force required to remove an implant, resonant frequency analysis and the torque required to remove the implant are all indicators of the level of osseointegration.

The term "enhancing bone repair", as used herein, refers to increasing the rate of new bone formation via bone remodeling, osteogenesis, osteoconduction and/or osteoinduction. The methods for enhancing bone repair in a mammal include those that stimulate bone formation and those that inhibit bone loss. The methods can thus be used for (1) providing an amount of a substance sufficient to act prophylactically to prevent the development of a weakened and/or unhealthy state; or (2) providing a sufficient amount of a substance to alleviate or eliminate a disease state and/or the symptoms of a disease state, and a weakened and/or unhealthy state.

The terms "osseous tissue" and "bone tissue", as used interchangeably herein, refer to the mineralized connective tissue that forms the major structural tissue of bones. Osseous tissue typically includes a collagen fiber matrix and deposited calcium salts in the form of hydroxyapatite. Osseous tissue includes compact bone tissue (found normally on the hard exterior of bones) and spongy bone tissue (found normally on the interior of bones). The major component of most human osseous tissue is hydroxyapatite (also known as hydroxylapatite, calcium hydroxide phosphate, calcium triphosphate, and tricalcium phosphate), $Ca_5(PO_4)_3OH$.

The term "mineralized connective tissue", as used herein, refers to biological tissues formed of a protein matrix that incorporates one or more minerals. The protein matrix in mineralized connective tissue may include collagen, elastin, gelatin, or combinations thereof. Examples of minerals found in mineralized connective tissue include hydroxyapatite, calcium carbonate, silica, calcium oxalate, whitlockite, and monosodium urate. Mineralized connective tissue may contain calcium salts, sodium salts, magnesium salts, etc. Examples of mineralized connective tissues include those found in bone, teeth, mollusc shells, deep sea sponge species, antler bone, tendon, cartilage, tooth enamel and dentin.

The term "teeth", as used herein, refers to natural teeth as well as artificial teeth or dental prosthesis.

The term "hydroxyapatite", as used herein, refers to a naturally occurring mineral form of calcium. Hydroxyapatite is also known as hydroxylapatite, calcium hydroxide phosphate, calcium triphosphate, and tricalcium phosphate. Hydroxyapatite has the chemical formula $Ca_5(PO_4)_3OH$, also sometimes written as $Ca_{10}(PO_4)_6(OH)_2$. The term "hydroxyapatite derivative", as used herein, refers to hydroxyapatite wherein one or more of the atoms or functional group has been replaced or modified. Although not necessarily the case, a hydroxyapatite derivative may be a compound that can be imagined to arise by chemical modification of hydroxyapatite. A hydroxyapatite derivative can include hydroxyapatite wherein one or more of the hydroxide (OH—) anions are substituted by another anion such as fluoride, chloride, bromide, carbonate, etc. A hydroxyapatite derivative can be fluorapatite or chlorapatite.

The term "metal," as used herein, refers to elemental metals, alloys of elemental metals, alloys having multiple components, and metals mixed with other elements or compounds in a heterogeneous or homogeneous mixture. Metals include titanium, hafnium, niobium, tantalum, chromium, vanadium, zirconium, cobalt, iron, alloys thereof, and combinations thereof. Metals can include stainless steels, and in particular surgical grade stainless steels. Metals may include oxides of the above metals, or metals having an oxide surface such as are generated when the metals are exposed to atmospheric oxygen.

The term "titanium", as used herein, refers to titanium, high purity titanium, commercial grade titanium, and titanium alloys including α-titanium alloys, β-titanium alloys, and α+β-titanium alloys. High purity titanium is substantially pure, having less than about 0.1% atomic impurities. Commercial grade titanium includes from about 0.1 to about 2% atomic impurities. Common impurities can include O, Fe, Pd, and other trace elements. Titanium, when exposed to oxygen, will generally have an oxide surface containing titanium (IV) oxides such as $TiO_2$ and to a lesser extent $Ti_2O_3$, $TiO$, and $Ti_3O_4$. Titanium alloys may include those described in U.S. Pat. No. 6,312,455; U.S. Pat. No. 6,258,182; U.S. Pat. No. 6,238,491; U.S. Pat. No. 5,690,670; U.S. Pat. No. 4,857,269; U.S. Pat. No. 6,183,508; and U.S. Pat. No. 6,767,418.

The term "α-titanium alloy", as used herein, refers to alloys of titanium containing one or more of Al, O, Zr, Sn, Mo, N, N, C, Ta, and Si. Exemplary α-titanium alloys include Ti-5Al-2.5Sn, Ti-8Al-1Mo-1N, and Ti-6Al-2Nb-1Ta-1Mo.

The term "β-titanium alloy", as used herein, refers to alloys of titanium containing relatively large amounts of Fe, N, Mo, Cr, Nb, W, Ta, and combinations thereof and smaller amounts of Al, O, Zr, Sn, Mo, N, V, C, Ta, Si, and combinations thereof. Exemplary β-titanium alloys include Ti-10N-2Fe-3Al, Ti-15Mo-5Zr-3Al, and Ti-13N-11Cr-3Al.

The term "α+β-titanium alloy", as used herein, refers to alloys of titanium containing Al, O, Zr, Sn, Mo, N, V, C, Ta, Si, and combinations thereof and β-stabilizing elements such as Fe, V, Mo, Cr, Nb, W, Ta, and combinations thereof. Exemplary α+β-titanium alloys include Ti-6Al-4N, Ti-6Al-2Sn-4Zr-2Mo, and Ti-6Al-2Sn-4Zr-6Mo.

The terms "bioactive agent" and "active agent", as used interchangeably herein, include, without limitation, physiologically or pharmacologically active substances that act locally or systemically in the body. A bioactive agent is a substance used for the treatment (e.g., therapeutic agent), prevention (e.g., prophylactic agent), diagnosis (e.g., diagnostic agent), cure or mitigation of disease or illness, a substance which affects the structure or function of the body, or pro-drugs, which become biologically active or more active after they have been placed in a predetermined physiological environment.

The terms "sufficient" and "effective", as used interchangeably herein, refer to an amount (e.g. mass, volume, dosage, concentration, and/or time period) needed to achieve one or more desired result(s).

The term "biocompatible", as used herein, refers to a material that along with any metabolites or degradation products thereof that are generally non-toxic to the recipient and do not cause any significant adverse effects to the recipient. Generally speaking, biocompatible materials are materials which do not elicit a significant inflammatory or immune response when administered to a patient.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

The term "pharmaceutically acceptable", as used herein, refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration. A "pharmaceutically acceptable carrier", as used herein, refers to all components of a pharmaceutical formulation which facilitate the delivery of the composition in vivo. Pharmaceutically acceptable carriers include, but are not limited to, diluents, preservatives, binders, lubricants, disintegrators, swelling agents, fillers, stabilizers, and combinations thereof.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

The term "small molecule", as used herein, generally refers to an organic molecule that is less than about 2000 g/mol in molecular weight, less than about 1500 g/mol, less than about 1000 g/mol, less than about 800 g/mol, or less than about 500 g/mol. Small molecules are non-polymeric and/or non-oligomeric.

The term "copolymer" as used herein, generally refers to a single polymeric material that is comprised of two or more different monomers. The copolymer can be of any form, such as random, block, graft, etc. The copolymers can have any end-group, including capped or acid end groups.

The term "hydrophilic", as used herein, refers to substances that have strongly polar groups that readily interact with water.

The term "hydrophobic", as used herein, refers to substances that lack an affinity for water; tending to repel and not absorb water as well as not dissolve in or mix with water.

The term "lipophilic", as used herein, refers to compounds having an affinity for lipids.

The term "amphiphilic", as used herein, refers to a molecule combining hydrophilic and lipophilic (hydrophobic) properties.

The term "mean particle size", as used herein, generally refers to the statistical mean particle size (diameter) of the particles in the composition. The diameter of an essentially spherical particle may be referred to as the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering. Two populations can be said to have a "substantially equivalent mean particle size" when the statistical mean particle size of the first population of nanoparticles is within 20% of the statistical mean particle size of the second population of nanoparticles; more preferably within 15%, most preferably within 10%.

The terms "monodisperse" and "homogeneous size distribution", as used interchangeably herein, describe a population of particles, microparticles, or nanoparticles all having the same or nearly the same size. As used herein, a monodisperse distribution refers to particle distributions in which 90% of the distribution lies within 5% of the mean particle size.

The term "targeting moiety", as used herein, refers to a moiety that binds to or localizes to a specific locale. The moiety may be, for example, a protein, nucleic acid, nucleic acid analog, carbohydrate, or small molecule. The locale may be a tissue, a particular cell type, or a subcellular compartment. The targeting moiety or a sufficient plurality of targeting moieties may be used to direct the localization of a particle or an active entity. The active entity may be useful for therapeutic, prophylactic, or diagnostic purposes.

The term "reactive coupling group", as used herein, refers to any chemical functional group capable of reacting with a second functional group to form a covalent bond. The selection of reactive coupling groups is within the ability of the skilled artisan. Examples of reactive coupling groups can include primary amines ($-NH_2$) and amine-reactive linking groups such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. Most of these conjugate to amines by either acylation or alkylation. Examples of reactive coupling groups can include aldehydes ($-COH$) and aldehyde reactive linking groups such as hydrazides, alkoxyamines, and primary amines Examples of reactive coupling groups can include thiol groups ($-SH$) and sulfhydryl reactive groups such as maleimides, haloacetyls, and pyridyl disulfides. Examples of reactive coupling groups can include photoreactive coupling groups such as aryl azides or diazirines. The coupling reaction may include the use of a catalyst, heat, pH buffers, light, or a combination thereof.

The term "protective group", as used herein, refers to a functional group that can be added to and/or substituted for another desired functional group to protect the desired functional group from certain reaction conditions and selectively removed and/or replaced to deprotect or expose the desired functional group. Protective groups are known to the skilled artisan. Suitable protective groups may include those described in Greene, T. W. and Wuts, P. G. M., Protective Groups in Organic Synthesis, (1991). Acid sensitive protective groups include dimethoxytrityl (DMT), tert-butylcarbamate (tBoc) and trifluoroacetyl (tFA). Base sensitive protective groups include 9-fluorenylmethoxycarbonyl (Fmoc), isobutyrl (iBu), benzoyl (Bz) and phenoxyacetyl (pac). Other protective groups include acetamidomethyl, acetyl, tert-amyloxycarbonyl, benzyl, benzyloxycarbonyl, 2-(4-biphenylyl)-2-propy!oxycarbonyl, 2-bromobenzyloxycarbonyl, tert-butyl, tert-butyloxycarbonyl, 1-carbobenzoxamido-2,2,2-trifluoroethyl, 2,6-dichlorobenzyl, 2-(3,5-dimethoxyphenyl)-2-propyloxycarbonyl, 2,4-dinitrophenyl, dithiasuccinyl, formyl, 4-methoxybenzenesulfonyl, 4-methoxybenzyl, 4-methylbenzyl, o-nitrophenylsulfenyl, 2-phenyl-2-propyloxycarbonyl, α-2,4,5-tetramethylbenzyloxycarbonyl, p-toluenesulfonyl, xanthenyl, benzyl ester, N-hydroxysuccinimide ester, p-nitrobenzyl ester, p-nitrophenyl ester, phenyl ester, p-nitrocarbonate, p-nitrobenzylcarbonate, trimethylsilyl and pentachlorophenyl ester.

II. Bone or Metal-Targeted Nanoparticles

Bone-targeted and metal-targeted nanoparticles can target bone, bone tissue, or bone minerals; can bind to bone, bone tissue, or bone minerals; can adhere to bone, bone tissue, or bone minerals; or a combination thereof. Bone-targeted nanoparticles can target, bind, and/or adhere to hydroxyapatite and hydroxyapatite derivatives, or to mineralized connective tissues, in particular to mineralized connective tissues containing calcium salts. Bone-targeted nanoparticles can target, bind, and/or adhere to teeth and dental implants. Metal-targeted nanoparticles can target, bind, and/or adhere to metals and metal alloys, such as titanium, hafnium, niobium, tantalum, chromium, vanadium, zirconium, cobalt, iron, alloys thereof, and oxides thereof, stainless steel, and titanium and titanium alloys including α-titanium alloys, β-titanium alloys, and α+β-titanium alloys.

The nanoparticles may have any desired size for the intended use. The nanoparticles may have any diameter from 10 nm to 1,000 nm. The nanoparticle can have a diameter from 10 nm to 900 nm, from 10 nm to 800 nm, from 10 nm to 700 nm, from 10 nm to 600 nm, from 10 nm to 500 nm, from 20 nm from 500 nm, from 30 nm to 500 nm, from 40 nm to 500 nm, from 50 nm to 500 nm, from 50 nm to 400 nm, from 50 nm to 350 nm, from 50 nm to 300 nm, or from 50 nm to 200 nm. In preferred embodiments the nanoparticles can have a diameter less than 400 nm, less than 300 nm, or more preferably less than 200 nm.

Figure 1B:
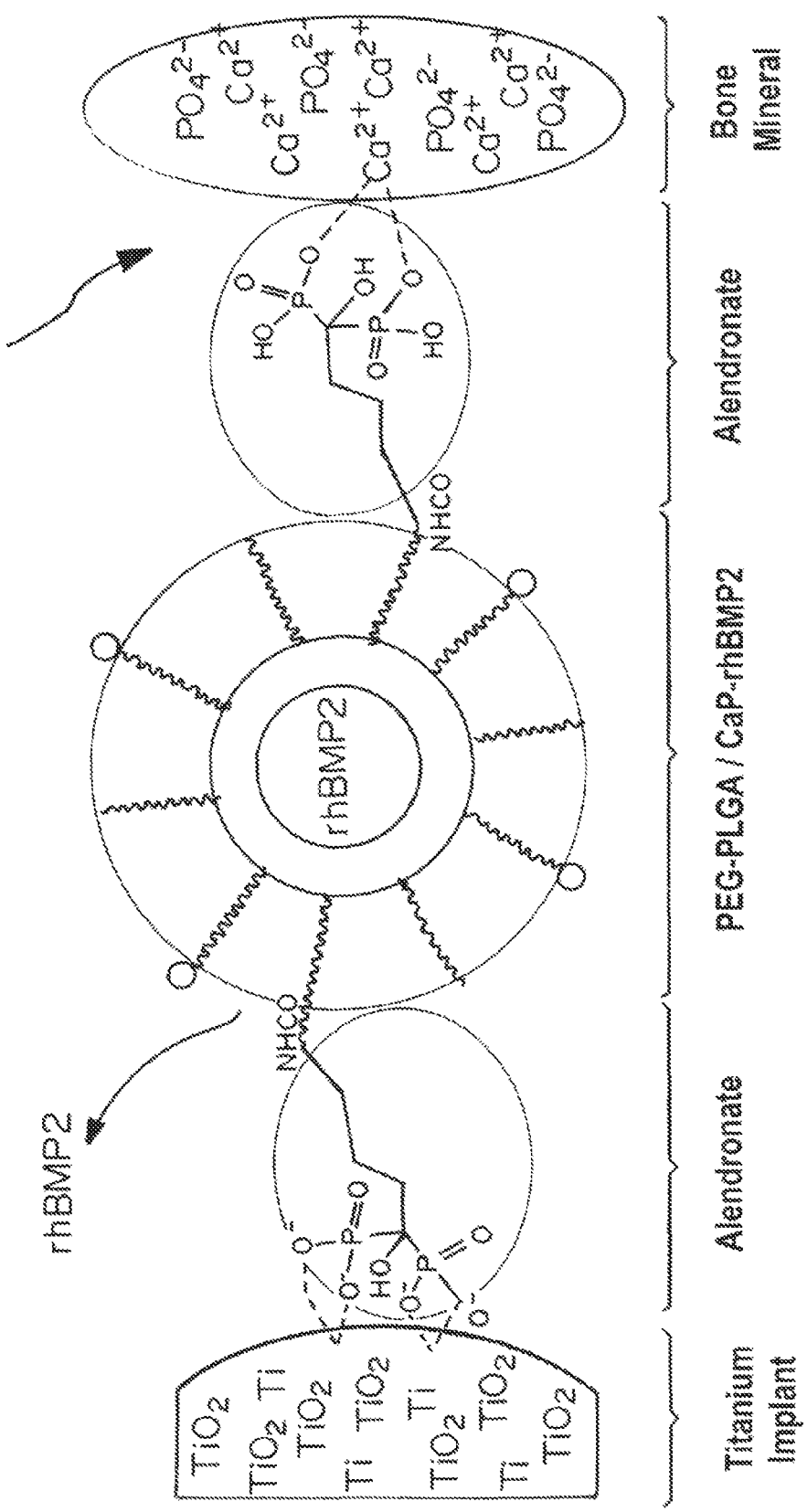
FIG. 1B is a diagram that reflects the mechanism of interaction of targeted nanoparticles with metal or bone mineral.

Representative polymeric nanoparticles contain a bone- or metal-targeting moiety that can selectively bind to bone, bone minerals, or metal ions and a biocompatible polymer. In some embodiments the nanoparticle has a targeting-moiety polymer conjugate that forms a hydrophilic outer layer and a hydrophobic inner core that can be loaded with one or more therapeutic agents (FIGS. 1A 1B). For example, suitable nanoparticles can contain PLGA-b-PEG-phosphonate in which the PEG-phosphonate component forms the hydrophilic outer shell and the PLGA component forms the hydrophobic inner core.

In some embodiments the nanoparticle has a core containing an inorganic salt and a protein, a hydrophilic outer layer, a hydrophobic layer intermediate to the core and the hydrophilic layer, and bone- or metal-targeting moieties on the surface. In some embodiments the hydrophobic layer may encapsulate a therapeutic, prophylactic, or diagnostic agent that is in addition to the protein in the core. For example, suitable nanoparticles may contain a protein/inorganic salt core surrounded by a PLGA-b-PEG-phosphonate conjugate forming the hydrophilic outer layer and the hydrophobic intermediate layer.

The targeting-moiety polymer conjugate can be blended with polymer to optimize the density of targeting ligands on the surface of the nanoparticle for improved targeting of the nanoparticle. Additionally, the ratio of target-element polymer conjugate to polymer can be optimized to increase the half-life of the nanoparticle in the blood of a subject.

A. Polymers

The nanoparticles can contain one more of the following polyesters: homopolymers including glycolic acid units, referred to herein as "PGA", and lactic acid units, such as poly-L-lactic acid, poly-D-lactic acid, poly-D,L-lactic acid, poly-L-lactide, poly-D-lactide, and poly-D,L-lactide, collectively referred to herein as "PLA", and caprolactone units, such as poly(ε-caprolactone), collectively referred to herein as "PCL"; and copolymers including lactic acid and glycolic acid units, such as various forms of poly(lactic acid-co-glycolic acid) and poly(lactide-co-glycolide) characterized by the ratio of lactic acid:glycolic acid, collectively referred to herein as "PLGA"; and polyacrylates, and derivatives thereof. Exemplary polymers also include copolymers of polyethylene glycol (PEG) and the aforementioned polyesters, such as various forms of PLGA-PEG or PLA-PEG copolymers, collectively referred to herein as "PEGylated polymers". In certain embodiments, the PEG region can be covalently associated with polymer to yield "PEGylated polymers" by a cleavable linker.

The nanoparticle can contain one or more hydrophilic polymers. Hydrophilic polymers include cellulosic polymers such as starch and polysaccharides; hydrophilic polypeptides; poly(amino acids) such as poly-L-glutamic acid (PGS), gamma-polyglutamic acid, poly-L-aspartic acid, poly-L-serine, or poly-L-lysine; polyalkylene glycols and polyalkylene oxides such as polyethylene glycol (PEG), polypropylene glycol (PPG), and poly(ethylene oxide) (PEO); poly(oxyethylated polyol); poly(olefinic alcohol); polyvinylpyrrolidone); poly(hydroxyalkylmethacrylamide); poly(hydroxyalkylmethacrylate); poly(saccharides); poly(hydroxy acids); poly(vinyl alcohol), and copolymers thereof.

The nanoparticle can contain one or more hydrophobic polymers. Examples of suitable hydrophobic polymers include polyhydroxyacids such as poly(lactic acid), poly(glycolic acid), and poly(lactic acid-co-glycolic acids); polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); polycarbonates such as tyrosine polycarbonates; polyamides (including synthetic and natural polyamides), polypeptides, and poly(amino acids); polyesteramides; polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), as well as copolymers thereof.

In certain embodiments, the hydrophobic polymer is an aliphatic polyester. In preferred embodiments, the hydrophobic polymer is poly(lactic acid), poly(glycolic acid), or poly(lactic acid-co-glycolic acid).

The nanoparticle can contain one or more biodegradable polymers. Biodegradable polymers can include polymers that are insoluble or sparingly soluble in water that are converted chemically or enzymatically in the body into water-soluble materials. Biodegradable polymers can include soluble polymers crosslinked by hydolyzable crosslinking groups to render the crosslinked polymer insoluble or sparingly soluble in water.

Biodegradable polymers in the nanoparticle can include polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl celluose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly (methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly (phenyl methacrylate), poly (methyl acrylate), poly(isopropyl acrylate), poly(isobutyl acrylate), poly(octadecyl acrylate), polyethylene, polypropylene poly(ethylene glycol), poly(ethylene oxide), poly (ethylene terephthalate), poly(vinyl alcohols), poly(vinyl acetate, poly vinyl chloride polystyrene and polyvinylpryrrolidone, derivatives thereof, linear and branched copolymers and block copolymers thereof, and blends thereof. Exemplary biodegradable polymers include polyesters, poly (ortho esters), poly(ethylene imines), poly(caprolactones), poly(hydroxybutyrates), poly(hydroxyvalerates), polyanhydrides, poly(acrylic acids), polyglycolides, poly(urethanes), polycarbonates, polyphosphate esters, polyphosphazenes, derivatives thereof, linear and branched copolymers and block copolymers thereof, and blends thereof. In particularly preferred embodiments the nanoparticle contains biodegradable polyesters or polyanhydrides such as poly(lactic acid), poly(glycolic acid), and poly(lactic-co-glycolic acid).

The nanoparticles can contain one or more amphiphilic polymers. Amphiphilic polymers can be polymers containing a hydrophobic polymer block and a hydrophilic polymer block. The hydrophobic polymer block can contain one or more of the hydrophobic polymers above or a derivative or copolymer thereof. The hydrophilic polymer block can contain one or more of the hydrophilic polymers above or a derivative or copolymer thereof. In preferred embodiments the amphiphilic polymer is a di-block polymer containing a hydrophobic end formed from a hydrophobic polymer and a hydrophilic end formed of a hydrophilic polymer. In some embodiments, a moiety can be attached to the hydrophobic end, to the hydrophilic end, or both.

In preferred embodiments the nanoparticles contain a first amphiphilic polymer having a hydrophobic polymer block, a hydrophilic polymer block, and a bone- or metal-targeting moiety conjugated to the hydrophilic polymer block; and a second amphiphilic polymer having a hydrophobic polymer block and a hydrophilic polymer block but without the bone- or metal-targeting moiety. The hydrophobic polymer block of the first amphiphilic polymer and the hydrophobic polymer block of the second amphiphilic polymer may be the same or different. Likewise, the hydrophilic polymer block of the first amphiphilic polymer and the hydrophilic polymer block of the second amphiphilic polymer may be the same or different.

B. Bone- and Metal-Targeting Moieties

The nanoparticles contain one or more targeting moieties that target bone, bone minerals, metals, or a combination thereof. Bone-targeting moieties can target the nanoparticle to bone, bone tissue, or bone minerals; can bind to the bone, bone tissue, or bone minerals; can adhere the nanoparticles to bone, bone tissue, or bone minerals; or a combination thereof. Bone-targeting moieties can target, bind, and/or adhere the nanoparticles to hydroxyapatite and hydroxyapatite derivatives. Bone-targeting moieties can target, bind, and/or adhere the nanoparticles to mineralized connective tissues, in particular to mineralized connective tissues containing calcium salts. Bone-targeting moieties can target, bind, and/or adhere the nanoparticles to teeth and dental implants. Metal-targeting moieties can target, bind, and/or adhere the nanoparticles to metals and metal alloys. Metal-targeting moieties can target, bind, and/or adhere the nanoparticles to titanium, hafnium, niobium, tantalum, chromium, vanadium, zirconium, cobalt, iron, and alloys thereof, and oxides thereof. Metal-targeting moieties can target, bind, and/or adhere the nanoparticles to stainless steel. Metal-targeting moieties can target, bind, and/or adhere the nanoparticles to titanium and titanium alloys including α-titanium alloys, β-titanium alloys, and α+β-titanium alloys.

The targeting moiety can be a calcium targeting moiety. The targeting moiety can be a calcium chelator. The targeting moiety can be a titanium targeting moiety. The targeting moiety can be a titanium chelator. The targeting moiety may chelate calcium, titanium, hafnium, niobium, tantalum, chromium, vanadium, zirconium, cobalt, iron, or combinations thereof.

The targeting moiety may be a di- or tri-carboxylic acid or a salt of a di- or tri-carboxylic acid. Suitable di- and tri-carboxylic acids include citric, tartaric, glutaric, malic, maleic or succinic acid. The targeting moiety may be a tetraacetic acid derived chelator such as ethylenediaminetetraacetic acid (EDTA); ethyleneglycol-bis(β-aminoethyl)-N,N,N',N'-tetraacetic Acid (EGTA); and 1,2-bis(2-aminophenoxy) ethane N,N,—N',N'-tetraacetic acid (BAPTA); and derivatives thereof.

The targeting moiety can be a phosphonate, for example a bisphosphonate. A preferred bisphosphonate is alendronate. In certain embodiments, the nanoparticles contain one or more different bisphosphonates. The bisphosphonate can be etidronate, clodronate, tiludronate, pamidronate, neridronate, olpadronate, alendronate, ibandronate, risedronate, zoledronate, or combinations thereof.

The targeting moiety can have the formula:

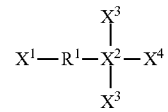

where $R^1$ is a $C_1$-$C_{30}$ linear or branched alkyl, substituted alkyl, alkenyl, substituted alkenyl, or alkylene oxide; $X^2$ is C, N, or Si; $X^4$ is none, OH, OCH$_3$, F, Cl, or Br; each $X^3$ is independently chosen from PO(OH)$_2$, PO(OR$^2$)(OH), PO(OR$^2$)$_2$, CH$_2$PO(OH)$_2$, CH$_2$PO(OR$^2$)(OH), CH$_2$PO (OR$^2$)$_2$, SO$_2$(OH), SO$_2$(OR$^2$), CH$_2$SO$_2$(OH), CH$_2$SO$_2$ (OR$^2$), NO$_2$, CH$_2$NO$_2$, B(OH)$_2$, CO(OH), and CH$_2$CO(OH); where each $R^2$ is independently $C_1$-$C_6$ alkyl or substituted alkyl; where $X^1$ is a reactive coupling group. In some embodiments $R^1$ is a $C_3$-$C_{15}$ linear or branched alkyl, substituted alkyl, alkenyl, substituted alkenyl, or alkylene oxide; $X^2$ is C or N; $X^4$ is OH or, when $X^2$ is N, none; $X^3$ is PO(OH)$_2$, PO(OR$^2$)(OH), or SO$_2$(OH); where $R^2$ is $C_1$-$C_3$ alkyl; and where $X^1$ is a reactive coupling group. In preferred embodiments $R^1$ is a $C_3$-$C_{15}$ linear or branched alkyl or substituted alkyl; $X^2$ is C; $X^4$ is OH; $X^3$ is PO(OH)$_2$; and $X^1$ is a reactive coupling group such as NH$_2$, COH, SH, isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, fluorophenyl esters, hydrazides, alkoxyamines, maleimides, haloacetyls, and pyridyl disulfides. In some embodiments R1 is methyl, ethyl, n-propyl, isopropyl, n-butyl, sec-butyl, or iso-butyl; $X^2$ is C; $X^4$ is OH or Cl; $X^3$ is PO(OH)$_2$; and $X^1$ is NH$_2$, isothiocyanate, isocyanate, acyl azide, NHS ester, sulfonyl chloride, aldehyde, glyoxal, epoxide, oxirane, carbonate, aryl halide, imidoester, carbodiimide, anhydride, or fluorophenyl ester.

C. Additional Moieties

The nanoparticles also contain one or more polymer conjugates containing end-to-end linkages between the polymer and a moiety. The moiety can be a targeting moiety, a detectable label, or a therapeutic, prophylactic, or diagnostic agent. For example, a polymer conjugate can be a PLGA-PEG-phosphonate. The additional targeting elements may refer to elements that bind to or otherwise localize the nanoparticles to a specific locale. The locale may be a tissue, a particular cell type, or a subcellular compartment. The targeting element of the nanoparticle can be an antibody or antigen binding fragment thereof, an aptamer, or a small molecule (less than 500 Daltons). The additional targeting elements may have an affinity for a cell-surface receptor or cell-surface antigen on a target cell and result in internalization of the particle within the target cell. Exemplary target cells include osteoclasts, osteoblasts, bone marrow cells, mesenchymal stem cells, or hematopoietic cells.

The nanoparticles can also contain a detectable label, such as, a radioisotope, a fluorophore (e.g., fluorescein isothiocyanate (FITC), phycoerythrin (PE)), an enzyme (e.g., alkaline phosphatase, horseradish peroxidase), element particles (e.g., gold particles) or a contrast agent.

In another embodiment, a fluorescent label is chemically conjugated to a polymer of the nanoparticle to yield a fluorescently labeled polymer. The polymer can be, but is not limited to, one or more of the following: PLA, PGA, PCL, their copolymers, polyacrylates, and the aforementioned PEGylated polymers.

In other embodiments the label is a contrast agent. A contrast agent refers to a substance used to enhance the contrast of structures or fluids within the body in medical imaging. Contrast agents are known in the art and include, but are not limited to agents that work based on X-ray attenuation and magnetic resonance signal enhancement. Suitable contrast agents include iodine and barium.

D. Polymer Ratios

The nanoparticles can contain one or a mixture of two or more polymers. The nanoparticles may contain other entities such as stabilizers, surfactants, or lipids. The nanoparticles may contain a first polymer having a bone- or metal-targeting moiety and a second polymer not having a bone- or metal-targeting moiety. By adjusting the ratio of the targeted and non-targeted polymers, the density of the targeting moiety on the exterior of the particle can be adjusted. In some embodiments the ratio is optimized to enhance the targeting and/or adhesion of the nanoparticle to the bone and/or metal.

The nanoparticles can contain an amphiphilic polymer having a hydrophobic end, a hydrophilic end, and a bone- or metal-targeting moiety attached to the hydrophilic end. In some embodiments the amphiphilic macromolecule is a block copolymer having a hydrophobic polymer block, a hydrophilic polymer block covalently coupled to the hydrophobic polymer block, and a bone- or metal-targeting moiety covalently coupled to the hydrophilic polymer block. For example, the amphiphilic polymer can have a conjugate having the structure A-B—X where A is a hydrophobic molecule or hydrophobic polymer, preferably a hydrophobic polymer, B is a hydrophilic molecule or hydrophilic polymer, preferably a hydrophilic polymer, and X is a bone- or metal-targeting moiety. Preferred amphiphilic polymers include those where A is a hydrophobic biodegradable polymer, B is PEG, and X is a bisphosphonate moiety that targets, binds, and/or adheres to bone or metal.

In some embodiments the nanoparticle contains a first amphiphilic polymer having the structure A-B—X as described above and a second amphiphilic polymer having the structure A-B, where A and B in the second amphiphilic macromolecule are chosen independently from the A and B in the first amphiphilic macromolecule, although they may be the same.

Figures 2A, 2B:
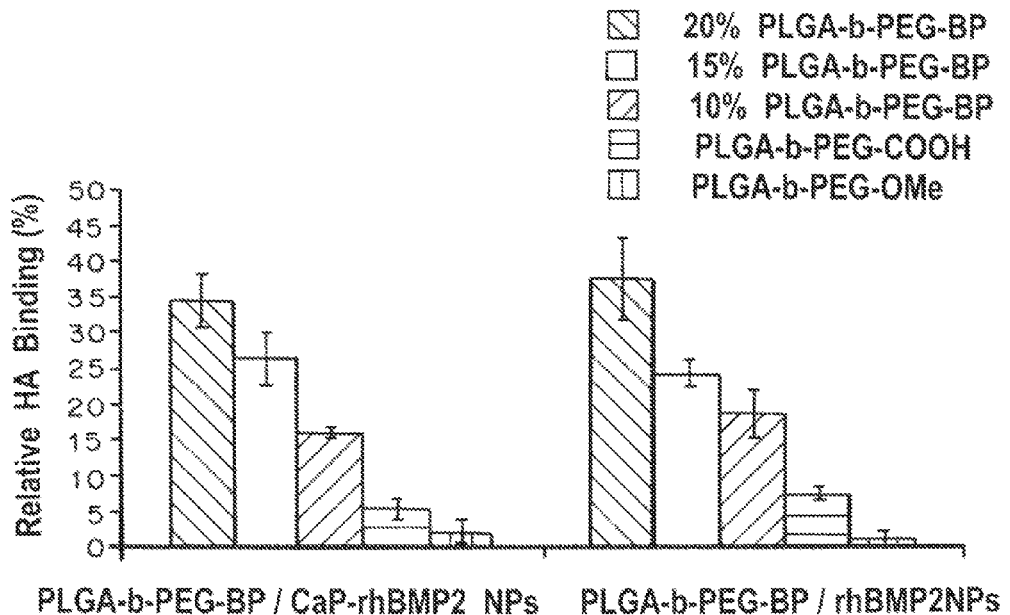
FIG. 2A is a bar graph of the relative binding to hydroxyapatite by PLGA-b-PEG-BP/CaP-rhBMP2 nanoparticles containing the following percentages of PLGA-b-PEG-BP going from left to right: 20%, 15%, 10%, 100% PLGA-b-PEG-COOH, or 100% PLGA-b-OMe.
FIG. 2B is a bar graph of the relative binding to hydroxyapatite by PLGA-b-PEG-BP/rhBMP2 nanoparticles containing the following percentages of PLGA-b-PEG-BP going from left to right: 20%, 15%, 10%, 100% PLGA-b-PEG-COOH, or 100% PLGA-b-OMe.
Figures 2C, 2D:
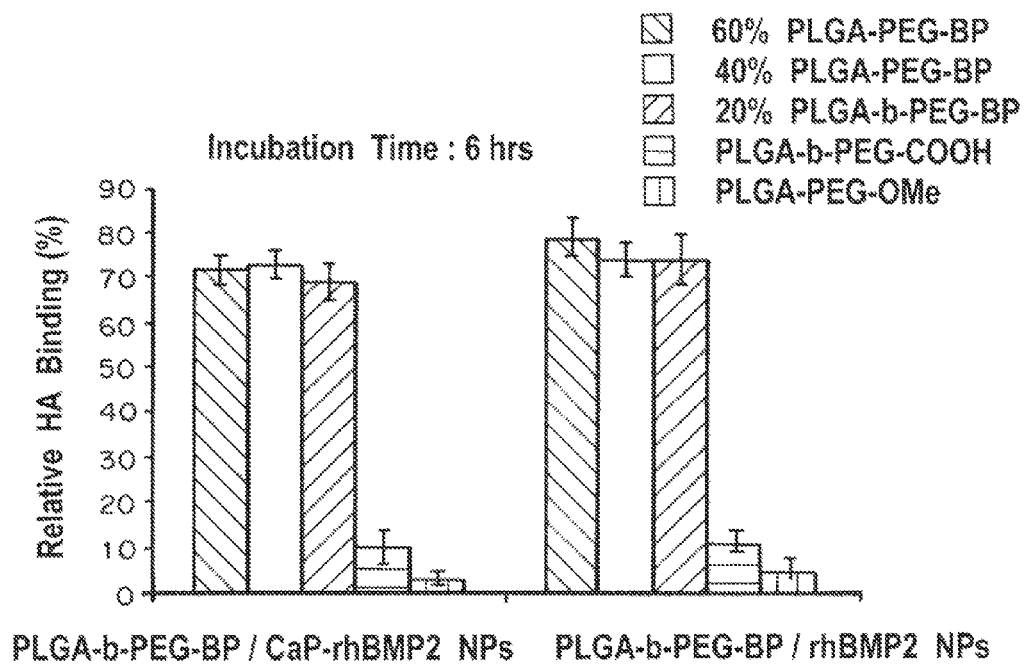
FIG. 2C is a bar graph of the relative binding to hydroxyapatite by PLGA-b-PEG-BP/CaP-rhBMP2 nanoparticles containing the following percentages of PLGA-b-PEG-BP going from left to right: 60%, 40%, 20%, 100% PLGA-b-PEG-COOH, or 100% PLGA-b-OMe.
FIG. 2D is a bar graph of the relative binding to hydroxyapatite by PLGA-b-PEG-BP/rhBMP2 nanoparticles containing the following percentages of PLGA-b-PEG-BP going from left to right: 20%, 15%, 10%, 100% PLGA-b-PEG-COOH, or 100% PLGA-b-OMe.
Figure 2E:
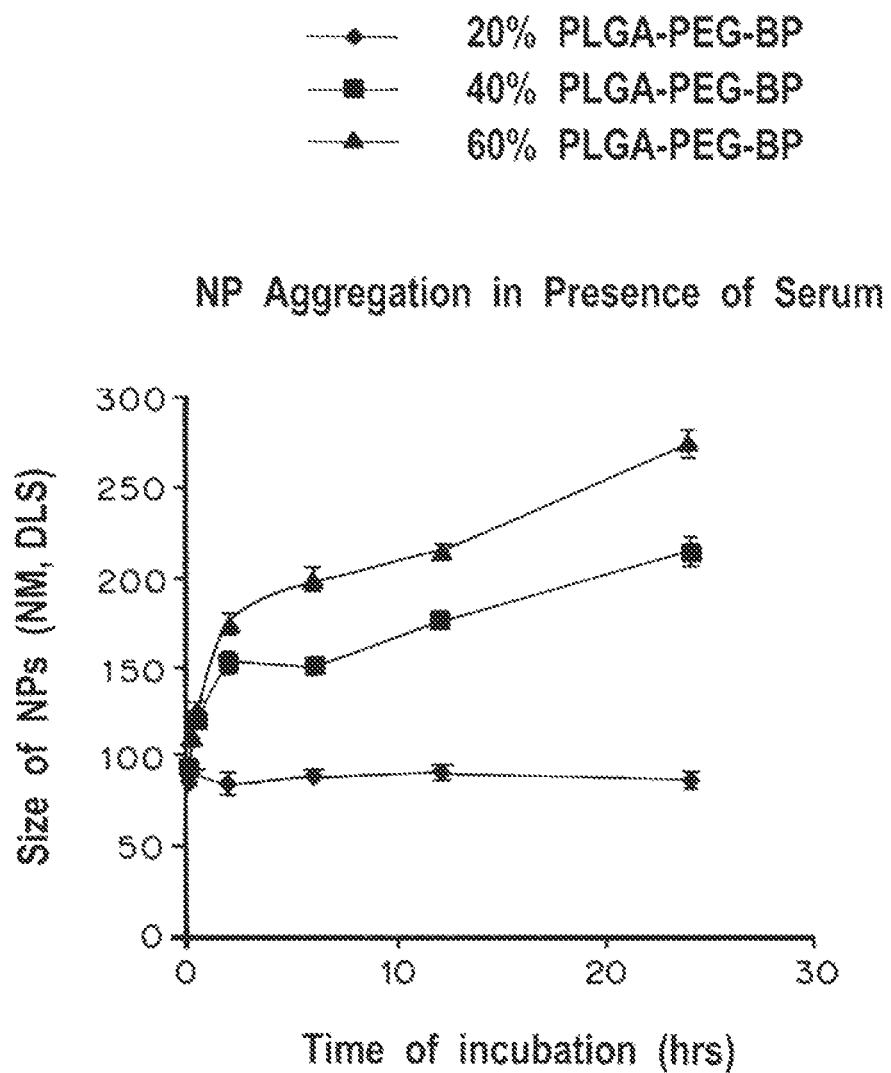
FIG. 2E is a line graph of size of nanoparticles (nm, dls) versus time of incubation (hours) of 20% PLGA-PEG-BP (♦); 40% PLGA-PEG-BP (■); and 60% PLGA-PEG-BP (▲).
Figure 3A:
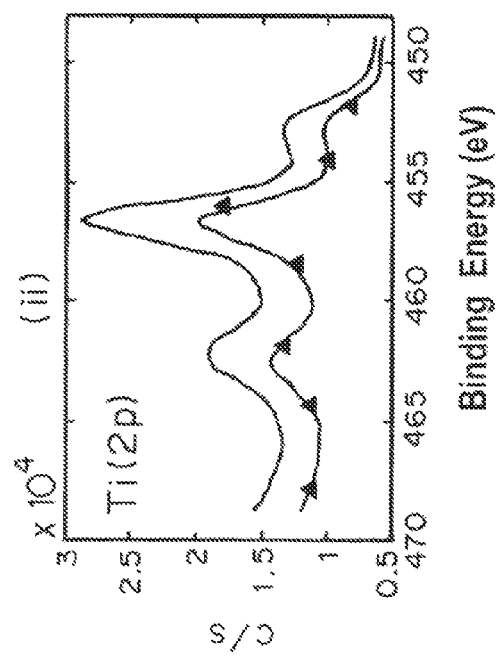
FIGS. 3A, 3B, 3C, 3D, 3E, 3F, 3G and 3H are panels of graphs (c/s versus binding energy, eV) showing elemental analysis of the surface of the metal implant dipped in NP solution and air dried thereafter, using X-ray Photoelectron Spectroscopy (XPS), by detecting titanium (Ti 2p), phosphorous (P2p), carbon (C1s) and oxygen (O1s) from $TiO_2$ and NPs. The left hand column graphs (for Ti, P, C, and O elemental analysis) are for implants dipped in PLGA-PEG-BP NPs solution (1 mg/ml in DI water) and right hand column graphs are elemental analysis of neat Ti implant surface (▲) or Ti implant dipped in non-targeted NPs (PLGA-PEG-COOH) solution. This graph confirms the PLGA-b-PEG-BP NPs coating on the Titanium implants after a quick dip in NP solution (1 mg/ml in DI water) due to the presence of phosphorous on the left column graphs and absence of the same on the right hand side column graphs, from NPs and implant surface.
Figure 3B:
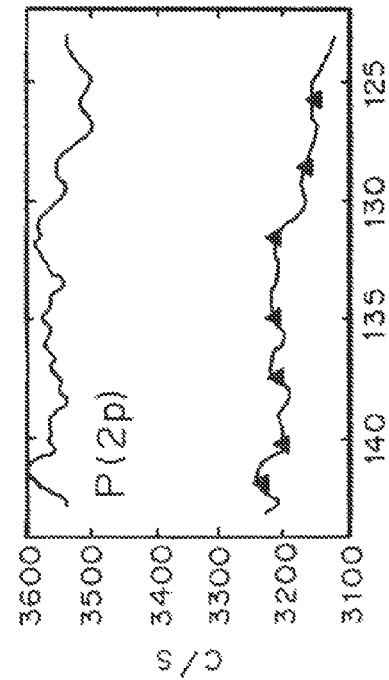
Figure 3C:
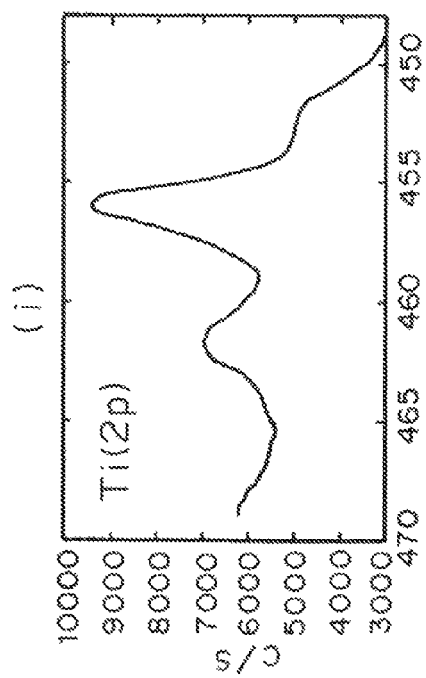
Figure 3D:
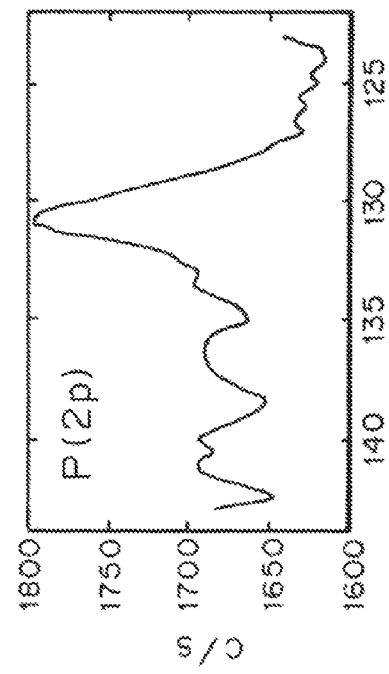
Figure 3F:
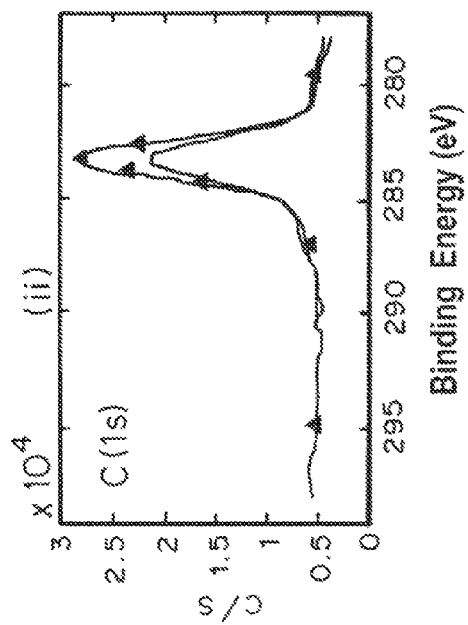
Figure 3H:
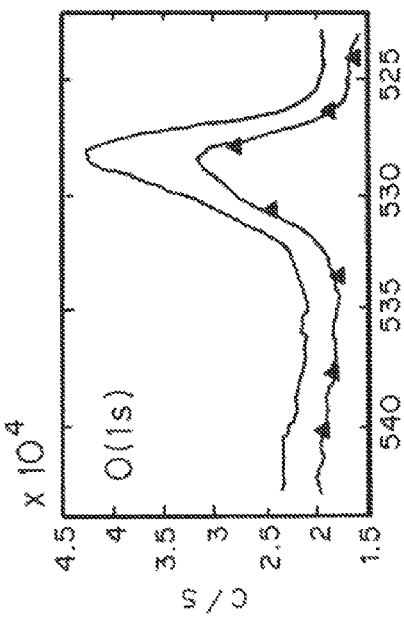
Figure 3E:
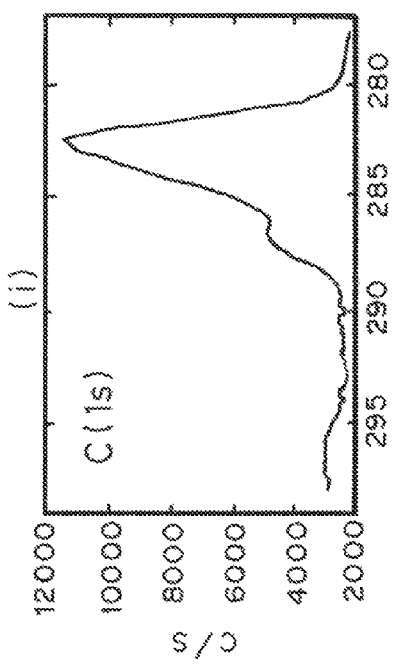
Figure 3G:
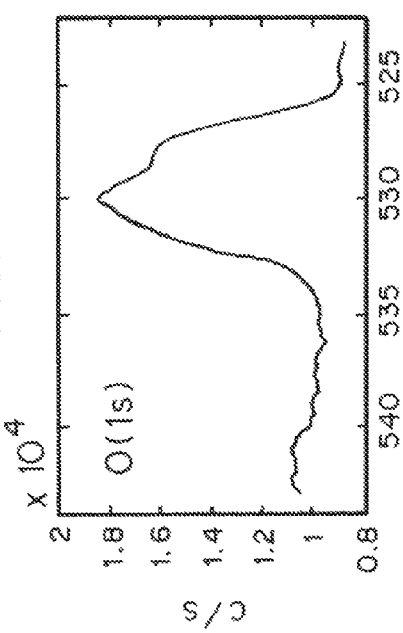
Figure 3I:
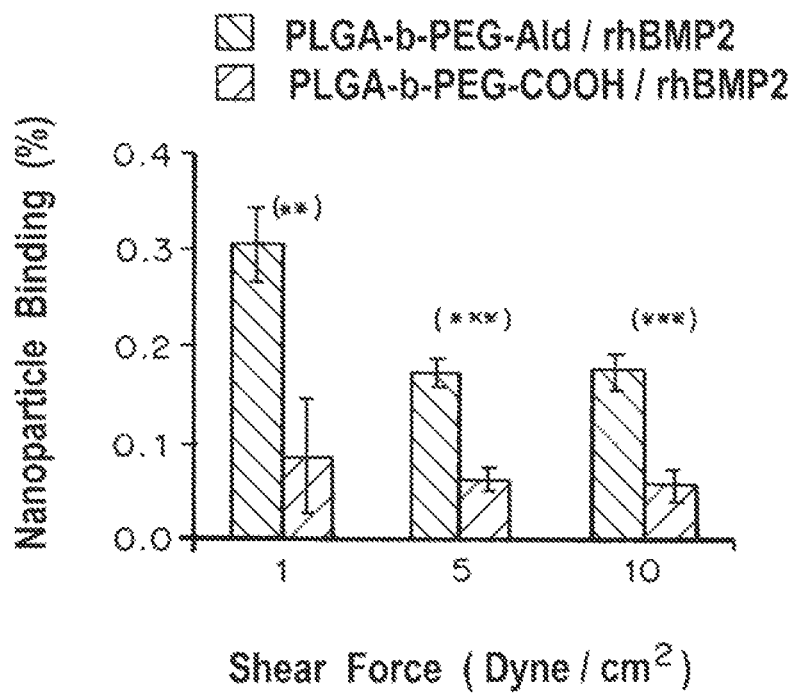
FIG. 3I is bar graph of nanoparticle binding (%) versus shear force ($Dyne/cm^2$) of PLGA-b-PEG-Ald/rhBMP2 (left of each pair) and PLGA-b-PEG-COOH/rhBMP2 (right of each pair)

One embodiment provides nanoparticles that are engineered to maximize half-life and targeting of the nanoparticles to bone, mineral, or metal ions by adjusting the amount of PEG and the density of bone, mineral, or metal ion specific ligand on the surface of the nanoparticles. As described in FIGS. 2A-2D, nanoparticles having 10%, 15%, 20%, 40% and 60% w/w target element-polymer conjugate with the balance made of the polymer itself showed significant targeting to hydroxyapatite. Thus, another embodiment provides nanoparticles having a ratio of target element-polymer conjugate to polymer from 1:9 to 2:3 that show significant targeting to bone. FIG. 2E shows that the nanoparticles of 20% PLGA-PEG-BP do not aggregate in serum and therefore would have an improved half-life in the blood of a subject.

E. Inner Core

The inner core of the nanoparticle can be hydrophobic and can be loaded with a therapeutic, prophylactic, or diagnostic agent. In some embodiments, the inner core contains a hydrophobic polymer such as poly(lactic acid), poly(glycolic acid), or poly(lactic acid-co-glycolic acid). In some embodiments the inner core contains an inorganic salt and a protein.

In some embodiments an inner core containing an inorganic salt is surrounded by an intermediate layer containing a hydrophobic polymer such as poly(lactic acid), poly(glycolic acid), or poly(lactic acid-co-glycolic acid).

1. Therapeutic Agent

The inner core can be loaded with one or more therapeutic agents such as a drug. Exemplary therapeutic agents include, but are not limited to, antibiotics, anti-inflammatory agents, chemotherapeutic agents, analgesics, hormones, steroids, cytotoxic agents, growth factors, cytokines, and combinations thereof The nanoparticles can be loaded with drugs, antibodies, or small molecules known in the art to treat one or more symptoms of cancer (collectively referred to as chemotherapeutic agents). Representative chemotherapeutic agents include, but are not limited to amsacrine, bleomycin, bortezomib, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ(2) and combinations thereof.

One or more growth factors or cytokines can be loaded into the nanoparticles. Preferred growth factors include, but are not limited to, bone morphogenic proteins. Bone morphogenic proteins include BMP-1, 2, 3, 4, 5, 6, 7, 8a, 8b, 10, and 15. A preferred bone morphogenic protein is BMP-2. Other growth factors include, but are not limited to, platelet derived growth factor (PDGF), erythropoietin (EPO), Myostatin (GDF-8), Nerve growth factor (NGF) and other neurotrophins, Thrombopoietin (TPO), Transforming growth factor alpha(TGF-α), Transforming growth factor beta (TGF-β), Tumor necrosis factor-alpha(TNF-α), Vascular endothelial growth factor (VEGF), Insulin-like growth factor (IGF), Fibroblast growth factor (FGF), Glial cell line-derived neurotrophic factor (GDNF), Granulocyte colony-stimulating factor (G-CSF), and Granulocyte macrophage colony-stimulating factor (GM-CSF).

The nanoparticles can also be loaded with one or more antibiotics. Suitable classes of antibiotics include, but are not limited to, aminoglycosides, ansamycins, carbacephem, carbapenems, cephalosporins, glycopeptides, lincosamides, lipopeptide, macrolides, monobactams, nitrofurans, oxazolidonones, penicillins, quinolones, sulfonamides, and tetracyclines. Specific antibiotics include, but are not limited to, Amikacin, Gentamicin, Kanamycin, Neomycin, Netilmicin, Tobramycin, Paromomycin, Spectinomycin, Geldanamycin, Herbimycin, Rifaximin, streptomycin, Loracarbef Ertapenem, Doripenem, 'Imipenem'/Cilastatin, Meropenem, Cefadroxil, Cefazolin, 'Cefalotin' or Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftaroline fosamil, Ceftobiprole, Clindamycin, Lincomycin, Daptomycin, Azithromycin, Clarithromycin, Dirithromycin, Erythromycin, Roxithromycin, Troleandomycin, Spiramycin, Aztreonam, Furazolidone, Linezolid, Posizolid, Radezolid, Torezolid, Amoxicillin, Ampicillin, Azlocillin, Cloxacillin, Dicloxacillin, Flucloxacillin, Mezlocillin, Methicillin, Nafcillin, Oxacillin, Penicillin G, Penicillin V, Piperacillin, Penicillin G, Ticarcillin, Amoxicillin/clavulanate, Ampicillin/sulbactam, Piperacillin/tazobactam, Ticarcillin/clavulanate, Timentin, Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfacetamide, Sulfadiazine, Silver sulfadiazine, Sulfadimethoxine, Sulfamethizole, Sulfamethoxazole, Sulfasalazine, Sulfisoxazole, Sulfamethoxazole, Demeclocycline, Doxycycline, Minocycline, Oxytetracycline, and Tetracycline.

In other embodiments, the nanoparticles can be loaded with oligonucleotides such as iRNA, RNA, DNA, and siRNA. The oligonucleotides can be single or double stranded. The oligonucleotides can be designed to inhibit or reduce the expression of targeted genes.

Still other embodiments provide nanoparticles loaded with two or more therapeutic agents described above.

In some embodiments the nanoparticle contains an inorganic salt. The inorganic salt can be a crystalline or semicrystalline inorganic salt. The inorganic salt can include calcium salts, sodium salts, potassium salts, magnesium salts, and aluminum salts. Inorganic salts can include phosphates, sulfates, pyrophosphates, citrates, and carbonates. Examples of inorganic salts can include calcium phosphate, calcium carbonate, calcium citrate, calcium sulfate, magnesium phosphate, magnesium sulfate, magnesium carbonate, or magnesium citrate. In some embodiments the inorganic salt is calcium phosphate. The inorganic salt may be encapsulated within a hydrophobic polymer core.

In some embodiments the inorganic salt forms part of an inorganic core, preferably encapsulating one or more therapeutic, prophylactic, or diagnostic agents. In preferred embodiments the inorganic core encapsulates a protein therapeutic agent, such as one of the growth factors described above. In some embodiments the nanoparticle has a core containing an inorganic salt and a protein therapeutic, surrounded by a biodegradable hydrophobic polymer shell (i.e. PLGA), surrounded by a hydrophilic polymer shell (i.e. PEG), having conjugated thereto a bone- or metal-targeting moiety. In some embodiments the nanoparticle core containing a protein and an inorganic salt has a diameter of less than 50 nm, less than 40 nm, less than 30 nm, or less than 25 nm. For example, the nanoparticle core containing an inorganic salt and a protein can have a diameter from 5 nm to 50 nm, from 5 nm to 40 nm, from 5 nm to 30 nm, from 10 nm to 30 nm, or about 20 nm.

Co-encapsulating a protein with an inorganic salt can increase the loading of the protein, increase the encapsulation efficiency of the protein, decrease the initial burst release of the protein from the nanoparticle, or a combination thereof. Nanoparticle containing an inorganic salt and a protein can have 10%, 20%, 30%, 40%, or 50% greater amount of protein encapsulated by weight as compared to nanoparticles prepared under similar conditions but without the inorganic salt. Nanoparticle containing an inorganic salt and a protein can have 10%, 20%, 30%, 40%, or 50% greater loading efficiency of protein as compared to nanoparticles prepared under similar conditions but without the inorganic salt. Nanoparticle containing an inorganic salt and a protein can have 20%, 30%, 40%, 50%, 60%, or 70% less burst release of protein (i.e. release within 12 hours, 18 hours, or 24 hours) as compared to nanoparticles prepared under similar conditions but without the inorganic salt. As demonstrated in Example 5, nanoparticles containing an inorganic salt and a protein exhibit much lower burst release, prolonged sustained release, and greater loading than analogous nanoparticle without the inorganic salt.

III. Methods of Making Bone- and Metal-Targeted Nanoparticles

A. Polymer Conjugates

Methods of polymer synthesis are described, for instance, in Braun et al. (2005) Polymer Synthesis: Theory and Practice. New York, N.Y.: Springer. The polymers may be synthesized via step-growth polymerization, chain-growth polymerization, or plasma polymerization.

In some embodiments an amphiphilic polymer is synthesized starting from a hydrophobic polymer terminated with a first reactive coupling group and a hydrophilic polymer terminated with a second reactive coupling group capable of reacting with the first reactive coupling group to form a covalent bond. One of either the first reactive coupling group or the second reactive coupling group can be a primary amine, where the other reactive coupling group can be an amine-reactive linking group such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. One of either the first reactive coupling group or the second reactive coupling group can be an aldehyde, where the other reactive coupling group can be an aldehyde reactive linking group such as hydrazides, alkoxyamines, and primary amines. One of either the first reactive coupling group or the second reactive coupling group can be a thiol, where the other reactive coupling group can be a sulfhydryl reactive group such as maleimides, haloacetyls, and pyridyl disulfides.

In preferred embodiments a hydrophobic polymer terminated with an amine or an amine-reactive linking group is coupled to a hydrophilic polymer terminated with complimentary reactive linking group. For example, an NHS ester activated PLGA can be formed by reacting PLGA-CO(OH) with NHS and a coupling reagent such as dicyclohexylcarbodiimide (DCC) or ethyl(dimethylaminopropyl) carbodiimide (EDC). The NHS ester activated PLGA can be reacted with a hydrophilic polymer terminated with a primary amine, such as a PEG-NH$_2$ to form an amphiphilic PLGA-b-PEG block copolymer.

In some embodiments a conjugate of an amphiphilic polymer with a bone- or metal-targeting moiety is formed using the same or similar coupling reactions. In some embodiments the conjugate is made starting from a hydrophilic polymer terminated on one end with a first reactive coupling group and terminated on a second end with a protective group. The hydrophilic polymer is reacted with a bone- or metal-targeting moiety having a reactive group that is complimentary to the first reactive group to form a covalent bond between the hydrophilic polymer and the bone- or metal-targeting moiety. For example, tBOC-PEG-NHS can be reacted with the primary amine on alendronate to form tBOC-PEG-b-Alendronate. The protective group can then be removed to provide a second reactive coupling group, for example to allow coupling of a hydrophobic polymer block to the conjugate of the hydrophilic polymer with the targeting moiety. In the example, tBOC-PEG-b-Alendronate may be deprotected with Tin (IV) Chloride to yield a primary amine terminated PEG, i.e. NH$_2$-PEG-b-Alendronate. A hydrophobic polymer terminated with a reactive coupling group complimentary to the second reactive coupling group can then be covalently coupled to form the conjugate. In the example, a PLGA-NHS can be reacted with the NH$_2$-PEG-b-Alendronate to form PLGA-b-PEG-Alendronate. Of course, the steps could also be performed in reverse order, i.e. a conjugate of a hydrophobic polymer and a hydrophilic polymer could be formed first followed by deprotection and coupling of the targeting moiety to the hydrophilic polymer block.

In some embodiments a conjugate is formed having a moiety conjugated to both ends of the amphiphilic polymer. For example, an amphiphilic polymer having a hydrophobic polymer block and a hydrophilic polymer block may have a bone- or metal-targeting moiety conjugated to the hydrophilic polymer block and an additional moiety conjugated to the hydrophobic polymer block. In some embodiments the additional moiety can be a detectable label. In some embodiments the additional moiety is a therapeutic, prophylactic, or diagnostic agent. For example, the additional moiety could be a moiety used for radiotherapy. The conjugate can be prepared starting from a hydrophobic polymer having on one end a first reactive coupling group and a another end first protective group and a hydrophilic polymer having on one end a second reactive coupling group and on another end a second protective group. The hydrophobic polymer can be reacted with the additional moiety having a reactive coupling group complimentary to the first reactive coupling group, thereby forming a conjugate of the hydrophobic polymer to the additional moiety. The hydrophilic polymer can be reacted with a bone- or metal-targeting moiety having a reactive coupling group complimentary to the second reactive coupling group, thereby forming a conjugate of the hydrophilic polymer to the bone- or metal-targeting moiety. The first protective group and the second protective group can be removed to yield a pair of complimentary reactive coupling groups that can be reacted to covalently link the hydrophobic polymer block to the hydrophilic polymer block.

B. Forming the Nanoaprticle Core

In some embodiments the nanoparticle core is a hydrophobic polymer core. The hydrophobic polymer core can be formed by nanoprecipitation of a hydrophobic polymer or using a microfluidic device. A hydrophobic polymer is dissolved in a water miscible organic solvent, optionally containing one or more therapeutic, prophylactic, or diagnostic agents to be encapsulated within the hydrophobic core. The resulting mixture solution is then added to polymer nonsolvent solution, such as an aqueous solution, to yield nanoparticles. In some embodiments the hydrophobic polymer core is formed by the hydrophobic polymer block of an amphiphilic polymer, preferably during the self-assembly of the amphiphilic polymer during the particle formation, such as by the emulsion and nanoprecipitation methods described below.

In some embodiments the nanoparticle core contains an inorganic salt. A nanoparticle core containing an inorganic salt can be formed by a slow crystallization from mixing two solutions containing precursors of the inorganic salt. Precursors of the inorganic salt can include the salts from strong acids or bases. For example, a salt precursor may include the ammonium salt of the anion and the halide of the cation, i.e. precursors for calcium phosphate could be calcium chloride and ammonium dihydrogen phosphate. The size of the inorganic core can be controlled by varying the concentration of the inorganic salt precursor solutions, varying the pH, varying the temperature, or by varying the speed and duration of mixing.

In some embodiments the inorganic salt has a therapeutic, prophylactic, or diagnostic effect. The nanoparticle core containing an inorganic salt can also encapsulate a therapeutic, prophylactic, or diagnostic agent. In preferred embodiments the nanoparticle core contains an inorganic salt and a protein, for example a growth factor. The therapeutic, prophylactic, or diagnostic agent can be dissolved in one or both of the solutions containing an inorganic salt precursor.

C. Emulsion Method

In some embodiments, the nanoparticle is prepared using an emulsion solvent evaporation method. For example, a polymeric material is dissolved in a water immiscible organic solvent. In some embodiments a solution of a therapeutic, prophylactic, or diagnostic agent to be encapsulated is mixed with the polymer solution. The polymer can be, but is not limited to, one or more of the following: PLA, PGA, PCL, their copolymers, polyacrylates, the aforementioned PEGylated polymers, the aforementioned block copolymers and polymer conjugates with bone- or metal-targeting moieties. The drug molecules can be, but are not limited to, one or a more of those discussed above as well as nuclear magnetic resonance (NMR) contrast agents, or combinations thereof. The water immiscible organic solvent, can be, but is not limited to, one or more of the following: chloroform, dichloromethane, and acyl acetate. The drug can be dissolved in, but is not limited to, one or more of the following: acetone, ethanol, methanol, isopropyl alcohol, acetonitrile and Dimethyl sulfoxide (DMSO). In some embodiments the polymer solution is blended with a solution containing the inorganic salt particle cores as described above, optionally encapsulating a therapeutic, prophylactic, or diagnostic agent.

In some embodiments the polymer solution contains one or more polymer conjugates as described above. The polymer solution can contain a first amphiphilic polymer conjugate having a hydrophobic polymer block, a hydrophilic polymer block, and a bone- or metal-targeting moiety conjugated to the hydrophilic end. In preferred embodiments the polymer solution contains one or more additional polymers or amphiphilic polymer conjugates. For example the polymer solution may contain, in addition to the first amphiphilic polymer conjugate, one or more hydrophobic polymers, hydrophilic polymers, lipids, amphiphilic polymers, polymer-drug conjugates, or conjugates containing other targeting moieties. By controlling the ratio of the first amphiphilic polymer to the additional polymers or amphiphilic polymer conjugates, the density of the bone- or metal-targeting moieties can be controlled. The first amphiphilic polymer may be present from 1% to 100% by weight of the polymers in the polymer solution. For example, the first amphiphilic polymer can be present at 10%, 20%, 30%, 40%, 50%, or 60% by weight of the polymers in the polymer solution.

An aqueous solution is then added into the resulting mixture solution to yield emulsion solution by emulsification. The emulsification technique can be, but not limited to, probe sonication or homogenization through a homogenizer. The therapeutic, prophylactic, or diagnostic agent may be associated with the surface of, encapsulated within, surrounded by, and/or distributed throughout the polymeric matrix of the particle.

D. Nanoprecipitation Method

In another embodiment, the nanoparticle is prepared using nanoprecipitation methods or microfluidic devices. A polymeric material or a blend of polymers is mixed, preferably in a water miscible organic solvent. A therapeutic, prophylactic, or diagnostic agent can be added to the polymer or polymer blend. In some embodiments a solution is added to the polymer or polymer blend with the nanoparticle core containing the inorganic salt as described above, optionally containing a protein or other therapeutic, prophylactic, or diagnostic agent.

The polymer can be, but is not limited to, one or more of the following: PLA, PGA, PCL, their copolymers, polyacrylates, the aforementioned PEGylated polymers, block copolymers and polymer conjugates with bone- or metal-targeting moieties. In some embodiments the polymer is a polymer conjugates as described above. In some embodiments the polymer blend contains one or more polymer conjugates as described above. The polymer blend can contain a first amphiphilic polymer conjugate having a hydrophobic polymer block, a hydrophilic polymer block, and a bone- or metal-targeting moiety conjugated to the hydrophilic end. In preferred embodiments the polymer blend contains one or more additional polymers or amphiphilic polymer conjugates. For example the polymer blend may contain, in addition to the first amphiphilic polymer conjugate, one or more hydrophobic polymers, hydrophilic polymers, lipids, amphiphilic polymers, polymer-drug conjugates, or conjugates containing other targeting moieties. By controlling the ratio of the first amphiphilic polymer to the additional polymers or amphiphilic polymer conjugates, the density of the bone- or metal-targeting moieties can be controlled. The first amphiphilic polymer may be present from 1% to 100% by weight of the polymers in the polymer blend. For example, the first amphiphilic polymer can be present at 10%, 20%, 30%, 40%, 50%, or 60% by weight of the polymers in the polymer blend.

The drug molecules can be, but are not limited to, one or more of the therapeutic agents discussed above as well as nuclear magnetic resonance (NMR) contrast agents, or combinations thereof. The water miscible organic solvent, can be, but is not limited to, one or more of the following: acetone, ethanol, methanol, isopropyl alcohol, acetonitrile and Dimethyl sulfoxide (DMSO).

The resulting mixture solution containing the polymer or polymer blend is then added to a polymer nonsolvent, such as an aqueous solution, to yield the nanoparticles.

IV. Formulations

The formulations contain an effective amount of nanoparticles in a pharmaceutical carrier appropriate for administration to an individual in need thereof to treat one or more symptoms of a disease or disorder. The formulations can be administered parenterally (e.g., by injection or infusion), enterally or mucosally, topically (spray, instillation) to an exposed bone or bone tissue, or as a component or coating on a device such as an implant or mixed with a cement, glue, or adhesive formulation.

Pharmaceutical formulations for parenteral administration are preferably in the form of a sterile aqueous solution or suspension of particles formed from one or more polymer-drug conjugates. Acceptable solvents include, for example, water, Ringer's solution, phosphate buffered saline (PBS), and isotonic sodium chloride solution. The formulation may also be a sterile solution, suspension, or emulsion in a nontoxic, parenterally acceptable diluent or solvent such as 1,3-butanediol.

A. Parenteral Formulations

The nanoparticles can be formulated for parenteral delivery, such as injection or infusion, in the form of a solution or suspension. The formulation can be administered via any route, such as, the blood stream or directly to the organ or tissue to be treated.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the nanoparticles can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s) or nanoparticles.

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the nanoparticles in the required amount in the appropriate solvent or dispersion medium with one or more of the excipients listed above, as required, followed by filtered sterilization. Generally, dispersions are prepared by incorporating the various sterilized nanoparticles into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the nanoparticle plus any additional desired ingredient from a previously sterile-filtered solution thereof.

In some instances, the formulation is distributed or packaged in a liquid form. Alternatively, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration may be buffered with an effective amount of buffer necessary to maintain a pH suitable for ocular administration. Suitable buffers are well known by those skilled in the art and some examples of useful buffers are acetate, borate, carbonate, citrate, and phosphate buffers.

Solutions, suspensions, or emulsions for parenteral administration may also contain one or more tonicity agents to adjust the isotonic range of the formulation. Suitable tonicity agents are well known in the art. Examples include glycerin, mannitol, sorbitol, sodium chloride, and other electrolytes.

Solutions, suspensions, or emulsions for parenteral administration may also contain one or more preservatives to prevent bacterial contamination of the ophthalmic preparations. Suitable preservatives are known in the art, and include polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for parenteral administration may also contain one or more excipients known art, such as dispersing agents, wetting agents, and suspending agents.

B. Enteral and Mucosal Formulations

The drug-encapsulated polymeric NPs can be further surface modified with the Fc portion of IgG. Fc receptor (FcRn) present on the apical membrane of absorptive epithelial cells predominately in the duodenum section of the small intestine. The FcRn is responsible for active transport of IgG antibodies across the intestinal epithelium through the process of transcytosis. Using the Fc portion of IgG to target drug-encapsulated polymeric NPs to the FcRn will allow drug-loaded NPs to be actively transported across the intestinal epithelium and enter systemic circulation after oral administration.

The nanoparticles can be administered in a suspension or as a dry powder to mucosal surfaces, including nasal, pulmonary, rectal, vaginal, and oral surfaces (for example, within for treatment of periodontal disease). Devices for mucosal and pulmonary delivery are well known.

C. Cements, Glues, and Adhesives

The bone- or metal-targeted nanoparticles can be prepared in a cement, glue, or adhesive formulation. The formulations can be applied directly to bone or bone injuries or applied to the surface of a medical or dental implant. Bone cements are provided as two-component materials. Bone cements consist of a powder (i.e., pre-polymerized PMMA and or PMMA or MMA co-polymer beads and or amorphous powder, radio-opacifer, initiator) and a liquid (MMA monomer, stabilizer, inhibitor). The two components are mixed and a free radical polymerization occurs of the monomer when the initiator is mixed with the accelerator. The bone cement viscosity changes over time from a runny liquid into a dough like state that can be safely applied and then finally hardens into solid hardened material. The set time can be tailored to help the physician safely apply the bone cement into the bone bed to either anchor metal or plastic prosthetic device to bone or used alone in the spine to treat osteoporotic compression fractures.

D. Dosage Regimens

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier.

V. Methods of Using Nanoparticles

The nanoparticles, nanoparticle formulations, and pharmaceutical compositions containing the nanoparticles can be used to treat diseases and disorders by targeted delivery of therapeutic agents to bone, mineral, or metal surfaces for the treatment of bone disorders or bone disease.

The terms "bone disease" and "bone related disorder", as used interchangeably herein, include injuries, diseases, and disorders of the bone tissue. Bone related disorders include diseases of bone formation or bone resorption. Bone related disorders include fractured bones, broken bones, chipped bones, and bone spurs. Additional bone related diseases include Bone cyst, Bone spur (Osteophytes), Bone tumor, Giant cell tumor of bone, Osteosarcoma, Craniosynostosis, Fibrodysplasia ossificans progressive, Fibrous dysplasia, Hypophosphatasia, Klippel-Feil syndrome, Metabolic Bone Disease, Osteitis deformans (or Paget's disease of bone), Osteitis fibrosa cystica (or Osteitis fibrosa, or Von Recklinghausen's disease of bone), Osteitis pubis, Condensing osteitis (or Osteitis condensans), Osteitis condensans ilii, Osteochondritis dissecans, Osteochondroma (Bone Tumor), Osteogenesis Imperfecta, Osteomalcia, Osteomyelitis, Osteopenia, Osteopetrosis, Porotic hyperostosis and Renal Osteodystrophy.

Bone diseases can include bone remodeling diseases such as osteoporosis, Paget's disease, renal osteodystrophy, renal rickets, osteoarthritis, rheumatoid arthritis, achondroplasia, osteochodrytis, hyperparathyroidism, osteogenesis imperfecta, congenital hypophosphatasia, fribromatous lesions, fibrous displasia, multiple myeloma, abnormal bone turnover, osteolytic bone disease and periodontal disease.

Bone related disorders can include achondroplasia, cleidocranial dysostosis, enchondromatosis, fibrous dysplasia, Gaucher's Disease, hypophosphatemic rickets, Marfan's syndrome, multiple hereditary exotoses, neurofibromatosis, osteogenesis imperfecta, osteopetrosis, osteopoikilosis, sclerotic lesions, pseudoarthrosis, pyogenic osteomyelitis, periodontal disease, anti-epileptic drug induced bone loss, primary and secondary hyperparathyroidism, familial hyperparathyroidism syndromes, weightlessness induced bone loss, osteoporosis in men, postmenopausal bone loss, osteoarthritis, renal osteodystrophy, infiltrative disorders of bone, oral bone loss, osteonecrosis of the jaw, juvenile Paget's disease, melorheostosis, metabolic bone diseases, mastocytosis, sickle cell anemia/disease, organ transplant related bone loss, kidney transplant related bone loss, systemic lupus erythematosus, ankylosing spondylitis, epilepsy, juvenile arthritides, thalassemia, mucopolysaccharidoses, Fabry Disease, Turner Syndrome, Down Syndrome, Klinefelter Syndrome, leprosy, Perthe's Disease, adolescent idiopathic scoliosis, infantile onset multi-system inflammatory disease, Winchester Syndrome, Menkes Disease, Wilson's Disease, ischemic bone disease (such as Legg-Calve-Perthes disease and regional migratory osteoporosis), anemic states, conditions caused by steroids, glucocorticoid-induced bone loss, heparin-induced bone loss, bone marrow disorders, scurvy, malnutrition, calcium deficiency, osteoporosis, osteopenia, alcoholism, chronic liver disease, postmenopausal state, chronic inflammatory conditions, rheumatoid arthritis, inflammatory bowel disease, ulcerative colitis, inflammatory colitis, Crohn's disease, oligomenorrhea, amenorrhea, pregnancy, diabetes mellitus, hyperthyroidism, thyroid disorders, parathyroid disorders, Cushing's disease, acromegaly, hypogonadism, immobilization or disuse, reflex sympathetic dystrophy syndrome, regional osteoporosis, osteomalacia, bone loss associated with joint replacement, HIV associated bone loss, bone loss associated with loss of growth hormone, bone loss associated with cystic fibrosis, chemotherapy-associated bone loss, tumor-induced bone loss, cancer-related bone loss, hormone ablative bone loss, multiple myeloma, drug-induced bone loss, anorexia nervosa, disease-associated facial bone loss, disease-associated cranial bone loss, disease-associated bone loss of the jaw, disease-associated bone loss of the skull, bone loss associated with aging, facial bone loss associated with aging, cranial bone loss associated with aging, jaw bone loss associated with aging, skull bone loss associated with aging, and bone loss associated with space travel.

A. Drug Delivery

1. Chemotherapeutic Agents

Chemotherapeutic agents discussed above can be delivered to bone by loading the described nanoparticles with one or more chemotherapeutic agents and administering the loaded nanoparticles with an amount effective to treat one or more symptoms of bone cancer. Dosages of the chemotherapeutic agent can be optimized by one skilled in the art.

2. Bone Inducing Factors

Bone remodeling can be influenced by delivering factors such as, bone inducing (osteoconductive, osteoinductive) and bone reducing agents using bone targeted nanoparticles loaded with drugs such as bone morphogenic proteins, in particular BMP-2 and administering them to a subject in need thereof in an amount effective to induce bone formation or growth. Typically, the BMP-2 is a recombinant protein available commercially. Thus, one embodiment provides a method for promoting bone growth or bone repair in a subject in need thereof by administering the nanoparticles containing a bone growth promoting agent such as a bone morphogenic protein (osteoinductive) and calcium phosphate (osteoconductive) in an amount effective to promote or induce bone growth or bone repair.

B. Osseointegration

Methods for promoting osseointegration are also provided. One embodiment provides a method for promoting the osseointegration of medical device into bone by coating the surface of the medical device with the nanoparticle and inserting or implanting the coated device into the bone. Typically, the nanoparticles are loaded with an agent that promotes or enhances bone growth. For example, the nanoparticles can be loaded with one or more bone morphogenic proteins as described above or with a combination of bone morphogenic proteins and a second therapeutic agent. The second therapeutic agent can be an osteoconductive agest (calcium phosphate), an antibiotic to prevent any infection, or an anti-cancer agent.

The medical device can be coated with the nanoparticles using conventional techniques including dip coating. Typically the device is metallic device. The device can contain titanium or a titanium alloy or other metal surfaces that can be coated with the nanoparticles. Representative medical devices include suture anchors, screws, pins, including locking pins, bone plates, interference screws, tacks, nails, fasteners, rivets, staples, medullary cavity nails, clips, clamps, tubes, tissue engineering scaffolds, rotator cuff repair devices, meniscus repair devices, guided tissue repair/regeneration devices, articular cartilage repair devices, tendon repair devices, ligament repair devices, fixation devices for an implant, plastic surgery devices (including devices for fixation of facial and breast cosmetic and reconstructive devices), fixation devices for surgical meshes, facial reconstructive devices, spinal fusion devices, devices for treatment of osteoarthritis, imaging devices, and bone graft substitutes.

C. Diagnostics

Another embodiment provides methods of diagnosing bone disorders or bone diseases by administering to host in need thereof, nanoparticles loaded with or having a detectable label. The detectable label can be attached to binding moiety that specifically binds to a target molecule, for example to a tumor antigen. Detection of the detectable label is correlated with the presence of the target molecule. The target molecule can be correlated to the presence of a disease or pathology, for example cancer. The amount of signal detected from the nanoparticles can be correlated to the presence or absence of a bone disorder or disease.

The present invention will be further understood by reference to the following non-limiting examples.

EXAMPLES

Example 1: Synthesis of PLGA-PEG-COOH and PLGA-PEG-Alendronate

Materials and Methods:
Reagents

The polymer Poly(D,L-lactide-co-glycolide) (50/50) with terminal carboxylate groups (PLGA, inherent viscosity 0.26-0.54 dl/g in hexafluoroisopropanol, MW 25 kDa) was obtained from Lactel Absorbable Polymers, USA. $NH_2$-PEG-COOH (MW 3400) and BOC—$NH_2$-PEG-COOH (MW 3400) were purchased from Laysan Bio, USA. All reagents were analytical grade or above and used as received, unless otherwise stated. The recombinant bone morphogenic protein (BMP) and BMP-2 Elisa kit was procured from R&D systems. Alkaline assay kit was purchased from LP assay Kit abCam. The alamar blue reagents, and Cy3-COOH, Alexa-NH2 dyes (647, 488, 405) was purchased by Invitrogen. The sodium alendronate, ascorbic acid, beta-gycerol phosphate, N-Hydroxysuccinimide (NHS), Ethyl-3-(3-dimethylaminopropyl) carbodiimide (EDC), hydroxy apatite, Alizarine red and any other chemicals were purchased from Sigma Aldrich. Bortezomib was purchased from Selleck.

Results

Carboxylate-functionalized copolymer PLGA-b-PEG was synthesized by amide conjugation of COOH-PEG-$NH_2$ to PLGA-COOH. In brief, PLGA-COOH was activated with EDC/NHS to produce PLGA-NHS in methylene chloride. This was precipitated out in an ice-cold mixture of ethyl ether and methanol. PLGA-NHS thus formed, after vacuum drying, was reacted with NH2-PEG-COOH in chloroform. The resulting copolymer was purified as described in previous step.

To synthesize $NH_2$-PEG-b-Alendronate, tBOC-PEG-NHS was stirred with alendronate (free acid form) in DMSO, at 1:1 molar ratio, for 6 hrs at room temperature. The reaction mixture was concentrated under vacuum and dropped in cold diethyl ether. After 1 h, at −20° C., the product, tBOC-PEG-Alendronate, was obtained, filtered and dried under vacuum. Further, tBOC-PEG-Alendronate (anhydrous dichloromethane) was stirred at RT for 1 h, with Tin (IV) Chloride (5 mmol) under anhydrous conditions, for boc de-protection. Excess of Tin (IV) chloride was removed under vacuum. $NH_2$-PEG-Alendronate was purified as described above. PLGA-b-PEG-Alendronate was synthesized by conjugation of $NH_2$-PEG-Alendronate to PLGA-COOH by using EDC and NHS to activate PLGA-COOH, as described above. The polymer conjugation was characterized by HPLC and TLC.

Example 2: Formulation of Bone Targeted and Non-Targeted PLGA-b-PEG-Ald and PLGA-b-PEG-Ald/CaP NPs Materials and Methods Nanoparticles (NPs) were prepared by nanoprecipitation and emulsion methods. In brief, Ald-PEG-PLGA (10 mg/ml, in acetonitrile) was mixed with therapeutic molecules (in DMSO) just before NP formation. NPs were formed by adding polymer-drug mixture dropwise into water to give a final concentration of 1 mg/ml. NPs were stirred for 4 hrs.

In the single emulsion method of Ald-PEG-PLGA NP formulation, 5 mg/ml of polymer blend of PLGA-PEG-BP to PLGA-PEG in a weight ratio of 1:5 (in chloroform) is mixed with a chemotherapeutic drug (e.g., Bortezomib) and emulsified with aqueous phase, using a probe sonicator for 90 to 120 seconds at 50 watt power for with pulses of 5 second on and intermediate 1 second stop time. The organic to aqueous phase volume ratio was between, 1:8 to 1:15. The emulsions were stabilized by adding polyvinyl alcohol (0.2%) to the aqueous phase. The NP emulsions were then stirred at room temperature for 4 to 6 hrs.

In a different drug formulation the synthesis is described in brief as following. A blend of PLGA-PEG-Ald to PLGA-PEG in a weight ratio of 1:1 of PLGA-b-PEG-COOH and PLGA-b-PEG-Ald (10 mg/ml, in acetonitrile) was mixed with rhBMP-2 protein (0.1 mg/ml, in water) just before NP formation (in a ratio of 1.25 mg rhBMP-2 per mg of polymer) and was added dropwise into water stirring at 600 rpm to give a final concentration of 1 mg/ml of NPs. The NPs were stirred at 600 rpm at RT for 2 hrs.

To prepare PLGA-b-PEG-Ald/Calcium Phosphate (PLGA-b-PEG-Ald/CaP) NPs, a freshly prepared CaP-rh-BMP2 nanocrystal solution (0.1 mg/ml, in water) was added to a blend of PLGA-b-PEG-COOH and PLGA-b-PEG-Ald polymers and the mixture was added dropwise—into water to form NPs encapsulating CaP-rhBMP2. Calcium Phosphate/rhBMP-2 nanocrystals are formed instantaneously by and gently mixing ammonium dihydrogen phosphate (15 µl, 110 mM, pH 9.0) with a mixture of Calcium Chloride (5 µl, 250 mM, pH 9.0) and rhBMP-2 (30 ul, 167 µg/ml, pH 6), at room temperature. The NPs were purified and concentrated as described above. The surface ligand density of Ald on NP was changed from 10% to 60% by blending PLGA-b-PEG-COOH and PLGA-b-PEG-Ald polymers in different weight ratios of 1:9 to 2:3.

The NPs were concentrated and purified from the traces of organic solvent, excess polymers and unencapsulated drug was removed by washing the NPs three times by using an Amicon centrifugation filtration membrane with a molecular mass cut-off of 100 kDa.

Size and Zeta

The Hydrodynamic diameter and surface charge (zeta potential, mV) of NPs were determined by Quasi-elastic laser light scattering using a ZetaPALS dynamic light scattering (DLS) detector (Brookhaven Instruments, Holtsville, N.Y.) in 20 mM isotonic 4-(2-hydroxyethyl) piperazine-1-ethanesulfonic acid (HEPES) buffer saline, pH 7.4 at RT.

The transmission electron microscopy (TEM) images of NPs and calcium phosphate nanocrystals were obtained using JEOL 2011 instrument at an accelerated voltage of 80 kV. The sample was prepared by depositing 10 µl of NP suspension (0.1 mg/ml) onto a 300-mesh carbon coated copper grid. Samples were blotted away after 5 to 10 min incubation, dried and allowed it to dry in vacuum. When needed the grids were counter-stained with 1% uranyl acetate.

Results

The PLGA-b-PEG-Ald and PLGA-b-PEG-Ald/CaP NPs encapsulating rhBMP-2 or chemotherapeutic drugs such as bortezomib were synthesis by emulsion and nanoprecipitation methods of formulations. In order to improve the therapeutic molecule loading and encapsulation efficiency as well as the release kinetics properties from PLGA-b-PEG- Ald NPs (FIG. 9) various techniques were used such as tuning the PLGA content in the NPs, increasing the initial drug load, optimizing the formulation conditions with respect aqueous to organic phase ratio, sonication power, time duration of sonication, and also co-precipitating rhBMP2 (a growth factor) with calcium phosphate (CaP) to form aqueous suspension of CaP-rhBMP2 nanostructures or nanocrystals. The formation of nanocrystals in the suspension depends on pH (7 to 9), temperature (25 to 37° C.), concentration of participating species ($Ca^{2+}$, $PO_4^{2-}$ and $rhBMP_2$) and time. The nanocrystal growth is faster at higher pH, temperature and concentration of calcium and phosphate ions. Appearance of faint turbidity in the solution confirms formation of the nanocrystals. The TEM shows that within the time range of 1 to 5 minutes the nanocrystals are in the size range of 20 nm and then continue to grow and aggregate. Addition of the CaP-rhBMP2 suspension to blend of polymers (PLGA-b-PEG, PLGA-b-PEG-Ald) checks aggregation, probably due to polymer coating and forms stable NPs with a core-shell structure. The stability of NPs was confirmed by DLS and TEM. TEM images show dense cores of CaP-rhBMP2 embedded in a 10-20 nm thick layer of polymer shell. The PLGA-b-PEG-Ald/CaP-rhBMP2 NPs were uniformly distributed over a size range of 90 to 110 nm with a hydrodynamic diameter of 130±20. The PLGA-b-PEG-Ald/rhBMP-2 NPs are 50 to 80 nm in size (TEM) with the hydrodynamic diameter in the range of 85±10 nm. Furthermore the zeta potential for all the NPs was close to neutral, in the range of 0 to −7 mV (Table 1).

Figure 4:
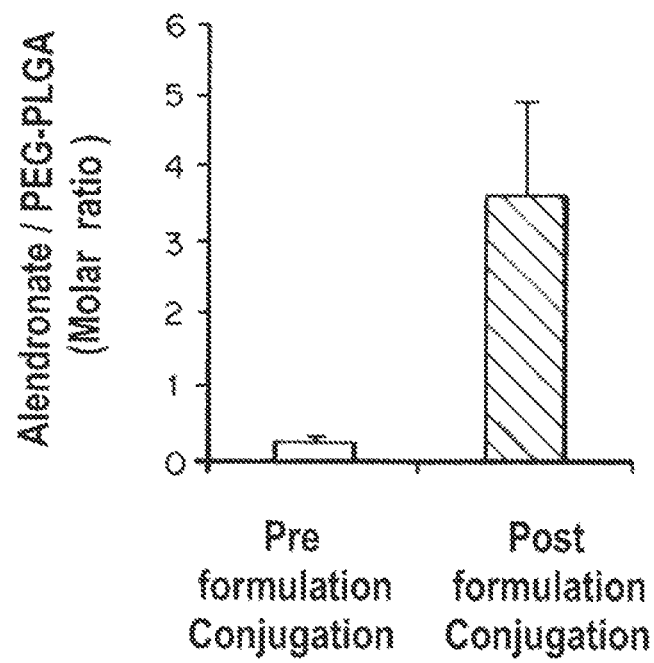
FIG. 4 is bar graph of alendronate/PEG-PLA (Molar ratio) of pre-formulation conjugation and post-formulation conjugation.

Characteristics of NPs having a CaPO4-rhBMP-2 core surrounded by a Ald-PEG-PLGA shell with Alendronate as targeting ligands on the NP surface are provided in Table 1. Alendronate content with the NPs by phosphate assay, where the post-formulation conjugation of alendronate on NP surface is compared to the pre-formulation conjugation is provided (FIG. 4). Transmission Electron Microscopy (TEM) images of Alendronate-PEG-PLGA/CaPO4-rhBMP-2 NPs, having a core-shell structure with CaPO4-rhBMP-2 cores were observed (data no shown). Uranyl acetate was used as a negative stain for the NPs.

TABLE 1

| Nanoparticle | Size (nm) ± Std Dev (PDI) | Zeta (mV) ± Std Dev |
|---|---|---|
| PLGA-b-PEG-Ald/rhBMP2 | 54 nm ± 3.7 (0.102) | −4.17 ± 1.1 |
| PLGA-b-PEG-Ald/CaP-rhBMP2 | 136 nm ± 4.2 (0.005) | −3.04 ± 1.2 |
| PLGA-b-PEG-COOH/rhBMP2 | 81 ± 4.6 (0.112) | −3.89 ± 1.0 |
| PLGA-b-PEG-COOH/CaP-rhBMP2 | 129 nm ± 6.5 (0.057) | −5.11 ± 0.62 |
| PLGA-b-PEG-OMe/rhBMP2 | 75.8 nm ± 2.8 (0.011) | 1.27 ± 0.45 |

Example 3: Ratio of Alendronate to Polymer in the NPs

Materials and Methods

The ratio of alendronate to polymer in the NPs was determined by phosphate assay. The PLGA-b-PEG-Ald NPs (10 μl of 10 mg/ml NPs in water) were mixed with 60 μl of concentrated $H_2SO_4$ and 10 μl of $H_2O_2$ in glass tubes and was heated for 10 minutes at 200° C. Thereafter, 690 μl $Na_2S_2O_5$ (3 mg/ml) was added to the tubes and the samples were incubated at 100° C. for 5 minutes. This was followed by adding 200 μl of $(NH_4)_6Mo_7O_{24} \cdot 4H_2O$ (20 mg/ml) and 20 μl of ascorbic acid (100 mg/ml) to the glass tubes and incubate for another 10 minutes at 100° C. The absorbance of the sample solutions were determined at 820 nm and were used to determine the phosphate concentrations of the samples. The calibration curves were based on known concentrations of $Na_2HPO_4$ as standards. Non-targeted PLGA-PEG NPs were used as negative control.

Results

FIG. 4 shows the ratio of alendronate/PEG-PLGA in pre and post formulation conjugation. There was effective incorporation of the bisphosphonate using both pre and post formulation conjugation techniques. In case of the preformulation conjugation technique the tri-block of PLGA-PEG-BP was blended with PLGA-PEG in various weight ratios (1:9 to 2:3) to obtain the flexibility of fine-tuning the targeting ligand density on the nanoparticles surface. This technique gave the minimum batch to batch variation and superior control over the targeted nanoparticles formulations. In case of post-formulation conjugation technique the PLGA-PEG-COOH was formulated into nanoparticles, activated by EDC/NHS reaction post formulation and mixed with bisphosphonate ($NH_2$-terminated) to form amide bond and conjugate to the nanoparticle surface. There was higher bisphosphonate density on the surface of the post-formulation conjugation nanoparticles and practically no control over ligand density, with large variation ligand conjugation from in batch to batch of nanoparticles. Thus, in all other examples we used pre-formulation conjugation as the standard method of introducing targeting ligand to the nanoparticle surface.

Example 4: In Vivo, In Vitro and Ex Vivo Bone Mineral Binding

Materials and Methods

The affinity of alendronate conjugated NPs, (PLGA-b-PEG-Ald) encapsulating rhBMP-2, towards bone mineral and bone (ex-vivo) was investigated in comparison to non-targeted (PLGA-b-PEG-COOH) NPs. Fluorescent labeled, stable NPs (AF647 labeled, in PBS, pH 7.4) were incubated with hydroxyapatite (HA microparticles) in microfuge tubes (at RT) and stirred (Sanyo Orbital Incubator) for varying lengths of time (15 minutes, 2, 4, 6, 12 and 24 hrs). At the end of incubation time the HA microparticles and the NPs bound to them were settled down by spinning the samples at 800 rpm for 5 min. The binding affinity of targeted NPs (fluorescent labeled) was determined by measuring the decrease in the relative concentration of targeted NPs in the supernatant compared to the non-targeted NPs.

Affinity of PLGA-b-PEG-Ald NPs to bone mineral was further confirmed by TEM imaging of HA (nanoparticles) in solution phase after incubation with NPs (targeted and non-targeted). The samples were prepared as described above.

Specific binding of alendronate conjugated NPs (AF647 labeled) to ex-vivo bone (skull, mice, 2 mm×2 mm) as compared to PLGA-b-PEG-COOH was also investigated by imaging under fluorescent microscope. After incubation, the bone pieces were washed three times with PBS and imaged again.

NP affinity to metal implant surface was investigated by scanning electron microscope (SEM) of PLGA-b-PEG-Ald/rhBMP2 NPs attached to the Ti surface (cleaned) of the implant that was dipped in NP (1 mg/ml in PBS, 2 hr), washed, dried and coated with gold to visualize under high vacuum in SEM, where the image clearly show the attachment of NPs to the Ti surface.

Results

To determine whether the engineered, alendronate conjugated PLGA-PEG NPs are able to target bone to deliver a desired payload, fluorescent bio-distribution studies were conducted using IVIS Animals injected with non-targeted and targeted nanoparticles were unable to be differentiated from each other at 1 hour. Notably at 24 hours, mice injected with targeted nanoparticles show increased retaining nanoparticles. Upon further investigation with bone histology shown in FIG. 12, one can see that there were increased levels of NP accumulation at 24 hours for targeted nanoparticles in bone (femur and spine). Thus the targeted nanoparticles showed significance in binding compared to non-targeted nanoparticles at 24 hours. In summary, the in vivo biodistribution study compliments the in vitro (HA binding) (FIG. 2) and ex vivo bone binding data to highlight the potential in utilizing alendronate conjugated nanoparticles for bone targeting and drug delivery applications.

The affinity of NPs with Alendronate (a bisphosphonate) was further confirmed by X-ray photoelectron spectroscopy where the presence of elements such as Phosphorous on Ti sheets treated with PLGA-b-PEG-Ald and its absence when the Ti sheets were treated with PLGA-b-PEG-COOH NPs (FIGS. 3A, 3B, 3C, 3D, 3E, 3F, 3G and 3H). The strength of metal binding of PLGA-b-PEG-Ald NPs (fluorescent labeled with PLGA-Alexa$_{488}$) was evaluated by using sheer flow stress. The Alendronate conjugated NPs sticks strongly to the metal surface whereas the NPs without ligand are washed off. The affinity of NPs to metal (Ti) surface as tested under sheer stress conditions proves the feasibility of Titanium targeted NPs for drug delivery applications at the location of surgical implantation in the body, under conditions of blood flow (FIG. 31).

Example 5: Encapsulation and Release Kinetics of Proteins

Materials and Methods

To evaluate the release kinetics of drugs (protein, chemotherapeutic drugs, etc.) from the NPs, a NP solution (1 mg/ml, in PBS) was incubated at 37° C., in triplicates for varying time periods. In case of protein's release kinetics from nanoparticles, at each time points the NPs were spun down and the amount of protein in the supernatant was evaluated. rhBMP2 released from the NPs was also evaluated using Elisa assay. The assay was performed using manufacturer's protocol (R&D Systems). The encapsulation efficiency and protein loading of different NP formulations were also evaluated by using BCA assay.

Results

The ability of NPs to encapsulate protein (rhBMP2, Lysozyme and Bovine serum albumin), release kinetics of protein (FIGS. 5A and 5B, 6) and role of CaP in controlling the release of protein from NPs, was investigated using ELISA assay and micro BCA assay. The release kinetics of rhBMP2 from NPs was done by ELISA assay by measuring the concentration of released protein at different time points (FIGS. 5A and 5B). CaP enhanced the encapsulation efficiency and protein load in the NPs Table 2 and it significantly impacted the release profile of protein from NPs (FIGS. 5A and 5B). The typical burst release of PLGA-b-PEG-Ald/rhBMP2 NPs was reduced with addition of CaP (FIG. 5B). The ELISA assay also ensured that the protein released from NPs was not denatured and had its receptor binding ability unaltered.

TABLE 2

| Nanoparticle | Burst release (12 to 24 hrs) | Sustained release/day (%) | Encapsulation Efficiency (%) | Loading (μg/mg) |
|---|---|---|---|---|
| PLGA-b-PEG-Ald/rhBMP2 | High (40-60%) | 0.25-1 | 82 | 1.025 |
| PLGA-b-PEG-Ald/CaP-rhBMP2 | Low (15-20%) | 1-1.5 | 91 | 1.136 |

TABLE 3

| NP/Protein | Initial feed (μg/ml per mg of Polymer) | Protein encapsulated (μg/ml per mg of Polymer) | Drug Encapsulation Efficiency (%) | Drug Loading (mg/mg) (%) |
|---|---|---|---|---|
| PLGA-b-PEG-Ald/BSA | 15 | 8.02 | 53.46 | 0.80 |
| PLGA-b-PEG-Ald/CaP-BSA | 15 | 11.95 | 79.66 | 1.19 |
| PLGA-b-PEG-Ald/Lyso | 10 | 6.80 | 68.07 | 0.68 |
| PLGA-b-PEG-Ald/CaP-Lyso | 10 | 8.37 | 87.49 | 0.87 |

Figure 6B:
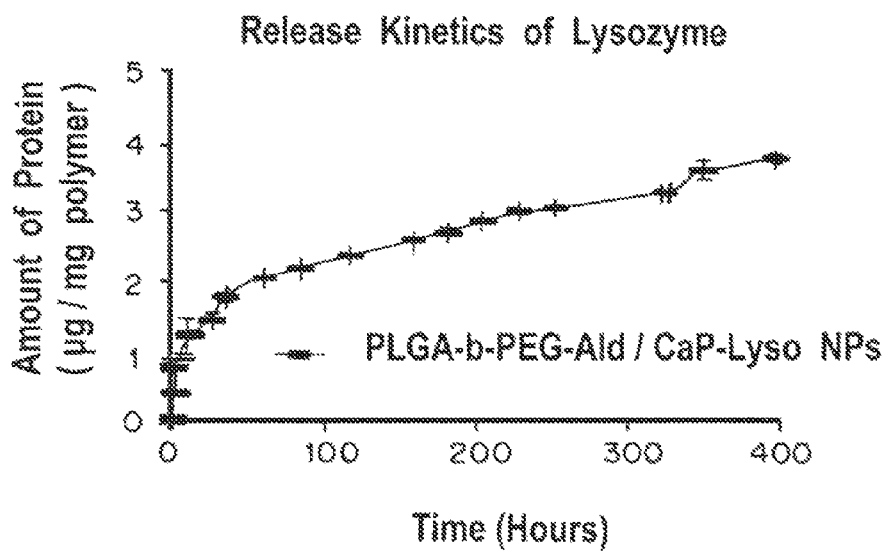
FIG. 6B is a line graph of lysozymer (µg/mg of polymer) released versus time (hours) for PLGA-b-PEG-Ald/CaP-Lyso NPs.

FIGS. 6A and 6B show the release kinetics of BSA or Lysozyme respectively.

Example 6: Encapsulation and Release Kinetics of Small Molecule Drugs

Materials and Methods

NPs were made as described encapsulating small model therapeutics, such as Bortezomib. In case of the small molecular drugs such as chemotherapeutic drugs, the NP solution (1 mg/ml, in PBS) was placed in a dialysis bag with suitable molecular weight cut-off range based on the drug used (eg., cut-off 3400 Da for Bortezomib). At each time point the nanoparticle were collected from the dialysis bag, dissolved in organic solvent (acetonitrile) to analyze for the encapsulated drug in nanoparticles using HPLC. At all time-points the buffer was replaced to maintain the sink conditions.

Results

Figure 9:
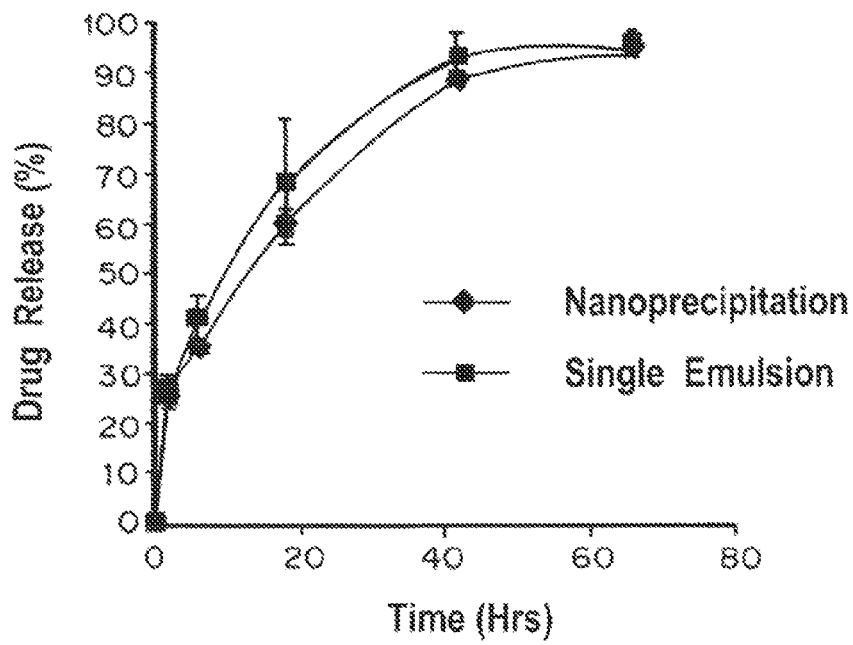
FIG. 9 is a line graph of Bortezomib release (%) versus time (hours) for nanoprecipitation (♦) and single emulsion (■) formed PLGA-b-PEG-Ald NPs.
Figure 10:
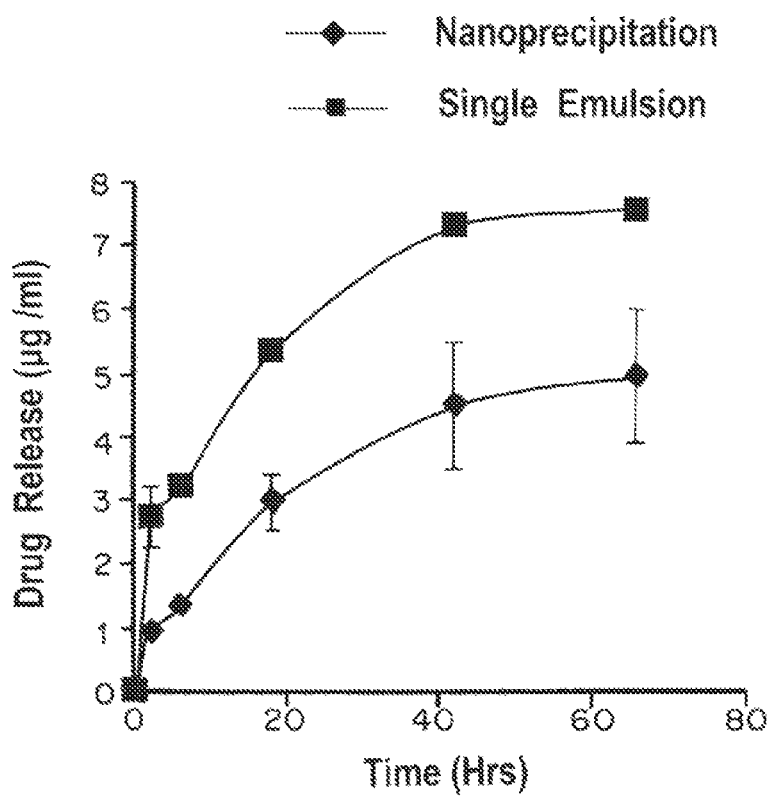
FIG. 10 is a line graph of Bortezomib release (µg/ml) versus time (hours) for nanoprecipitation (♦) and single emulsion (■) formed PLGA-b-PEG-Ald NPs.

The release kinetics of small molecular drugs (eg., bortezomib) from nanoparticles was analyzed by using two different formulation techniques: nanoprecipitatin and single emulsion. The drug was found to have an initial burst release followed by sustained release for several days (FIGS. 9 and 10).

Figure 7:
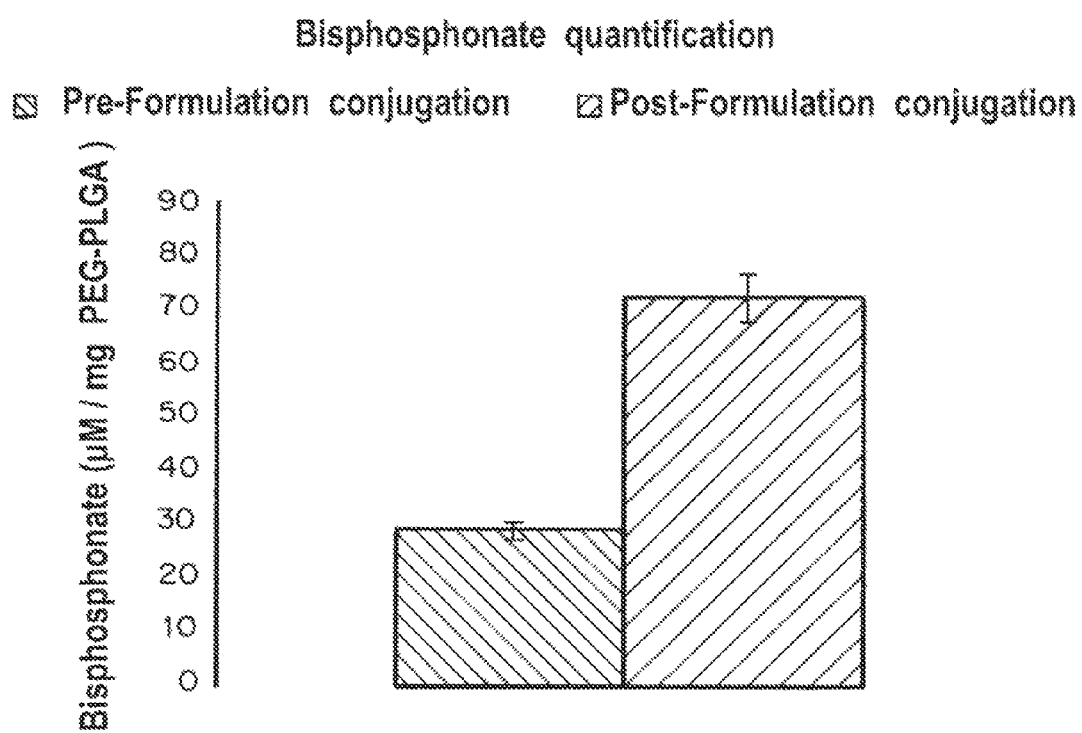
FIG. 7 is a bar graph showing bisphosphonate quantification for pre-formulation conjugation and post-formulation conjugation in (µM/mg PEG-PLGA).
Figure 8:
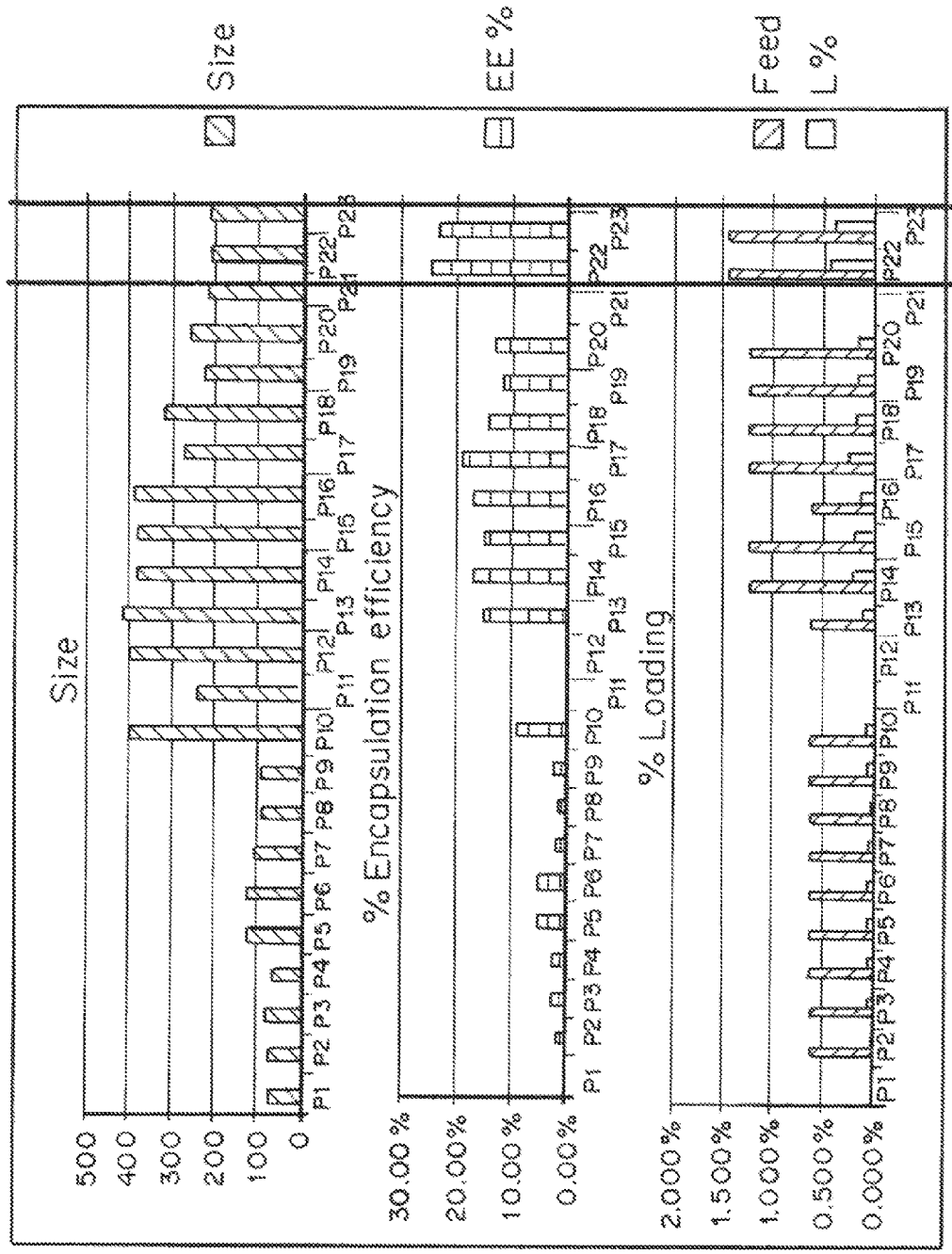
FIG. 8 is a panel of line bar graphs of size, percent encapsulation efficiency, and percent loading of Bortezomib for PLGA-b-PEG-Ald NPs.

TEM images of NPs made by the single emulsion formulation method were produced as described above. Table 4 shows the formulation physicochemical characterization of the PLGA-PEG-Ald NPs made by different formulations encapsulating bortezomib. FIG. 7 shows the quantification of Alendronate (Bisphosphonate) conjugation to the PLGA-b-PEG NPs. FIGS. 9 and 10 show the drug release kinetics (%) from NPs produce with the nanoprecipitation (♦) method or the single emulsion method (■) over time (hours).

TABLE 4

| Formulation Method | Size (PDI) | Zeta (mV) | Drug EE % | Drug Load % |
|---|---|---|---|---|
| Nano-precipitation | 73.8 nm (0.211) | −3.41 | 5.4% | 0.04% |
| Single Emulsion | 231 nm (0.274) | −2.36 | 24% | 0.5% |

Example 7: In Vitro Activity of the Released rhBMP-2

Materials and Methods
Cell Culture

The in vitro experiments were performed on bone marrow-derived human mesenchymal stem cells (hMSC, PT-2501, Lonza). hMSCs were cultured in normal growth media (POIETICS™ MSCGM™ BULLETKIT™ (PT-3001) Lonza), in 5% $CO_2$ at 37° C. The cells were cultured until 70-75% confluence and were used before passage 5 for all the experiments. The cells were trypsinized (CC-3232, Lonza) and seeded in 48-well plates at the density of 5000 cells/well in normal growth media. After 24 hours, the media was replaced with the normal and osteoconductive (supplemented with 10 nM β-glycerol phosphate and 50 μg/ml ascorbic acid). The osteoinductive media was made by supplementing rhBMP2 (free or NP loaded) to osteoconductive media so as to induce osteogenic differentiation of hMSCs. hMSCs grown in normal and osteoconductive media (without NPs) was used as negative controls.

ALP Quantification and Staining/Osteogenesis of hMSCs

In order to detect the alkaline phosphatase (ALP) activity induced by the rhBMP-2, the hMSCs were seeded in 48 well plates as described above and after 24 hrs incubation in the growth medium the cells were treated with rhBMP-2 loaded NPs in normal media and osteoconductive media conditions. At the end of each time points (0, 3, 5, 10, 14 and 21 days) the media was aspirated cells were washed with PBS and lysed as mentioned in previous section. The ALP activity in hMSCs was measured using a colorimetric endpoint assay (Alkaline Phosphatase Colorimetric Assay Kit (ab83369)), which quantified the conversion of p-nitrophenol phosphate (pNPP) to yellow p-nitrophenol (pNPP) by ALP enzyme. Briefly, cell lysate of the samples (80 ul) and the assay buffer solution of 5 mM pNPP (50 ul) were added to a 96-well plate. After 1 h of incubation, the absorbance was read at 405 nm in a microplate reader (microplate reader, BioTEK). A standard curve was made from standards (0-20 μM) prepared with a pNPP solution. Cells only and cells treated with empty NPs were used as negative control. Sample and standard triplicates were analyzed and sample concentrations read off from the standard curve. hMSCs treated with NPs were also stained with ALP staining reagent (Invitrogen) and were imaged using a Zeiss Discovery V8 Stereo Microscope (DISV8).

Alizarine Red S Staining

The hMSCs treated with various PLGA-b-PEG-Ald, PLGA-b-PEG-Ald/CaP, PLGA-b-PEG-Ald/CaP-rhBMP2, PLGA-b-PEG-Ald/rhBMP2 NP samples and suitable controls cells treated with free rhBMP2 and untreated cells were fixed with 4% formaldehyde as described previously at different time points (1, 7, 14, 21 and 21 days). After PBS wash (3×1 ml), fixed cell were washed with de-ionized water (3×1 ml) so as to remove any salt residues. The washed cells were treated with 0.5 ml of 2% Alizarin Red S (ARS, Sigma Aldrich, Germany) solution at pH 4.2, for 10 min. at room temperature. The excess of ARS was removed and washed with distilled water. The ARS staining was imaged using a Zeiss Discovery V8 Stereo Microscope (DISV8).

Alizarine Red S Quantification

In order to quantify the orange-red coloration of ARS, 10% acetic acid (Sigma Aldrich, Germany) was added to the cells. After an overnight incubation, the cells with the acetic acid were transferred to tubes and centrifuged for 15 minutes at 20,000×g. The supernatant was removed to other tubes and neutralized with ammonium hydroxide, 10% (Sigma Aldrich, Germany). 100 μL of each sample was added to 96-well plates and the OD405 was read using an Epoch microplate reader (Biotek, USA).

Immunocytochemistry

Cells were cultured in normal and osteoconductive (OC) media in the presence of rhBMP2 loaded NPs as described above. After 21 days of addition of NPs, cells were fixed with 4% formaldehyde for 15 min at room temperature, washed with (3×1 ml) PBS. Cells were permeabilized with 0.1% triton X100 in PBS and further incubation with 10% bovine serum albumin to block nonspecific binding of antibodies. Treated cells were then incubated with primary antibodies (24 hour at 4° C.): mouse monoclonal, anti-human osteocalcin mouse monoclonal (1:100 dilution, Abcam CAT No: ab69498) and anti-human osteopontin mouse monoclonal (1:100 dilution, Abcam CAT No: ab69498). Thereafter, cells were washed with PBS (3×1 ml) and incubated for one hour with the appropriate secondary antibody, either AF488 rabbit anti-mouse (IgG) (Invitrogen, USA), or AF594 goat anti-mouse (IgG) diluted 1:100. Negative control samples were not subjected to primary antibody incubation Immunolabeling was qualitatively analyzed the using Nikon Eclipse TE2000-U fluorescence microscope (Japan) equipped with FITC filter (ex: 450-505 nm; polychromatic mirror: 510-555 nm; barrier filter: 515-545 nm) and FITC-Texas Red filter (ex: 560-580 nm; polychromatic mirror: 585-665 nm; barrier filter: 600-650 nm).

Results

The functionality of the protein delivered by NPs was assessed by investigating the bioactivity of rhBMP2 loaded NPs in hMSCs, by determining induction of ALP enzymatic activity, calcification and expression of osteogenic proteins such as osteocalcin and osteopointin.

Figure 11A:
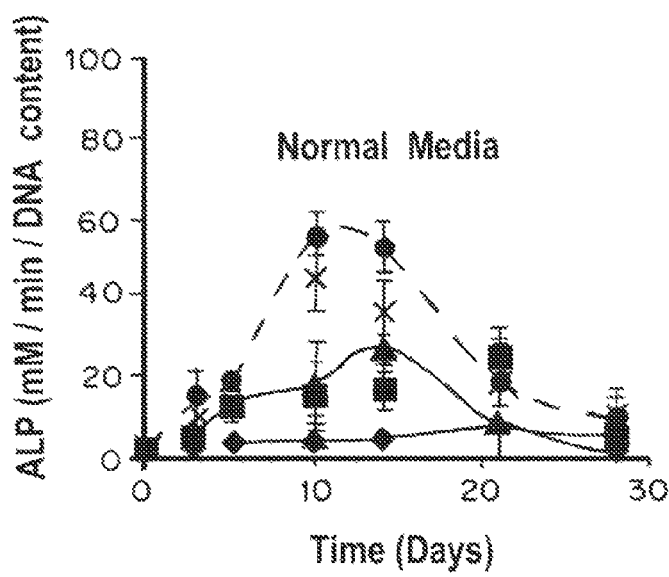
FIG. 11A is a line graph of ALP (mM/min/DNA content) versus time (days) of bone marrow-derived human mesenchymal stem cells in normal media treated as indicated (free rhBMP2, Day 1) (♦); PLGA-b-PEG-Ald/CaP (▲); PLGA-b-PEG-Ald/CaP-rhBMP2 (●); PLGA-b-PEG-Ald (■); and PLGA-b-PEG-Ald/rhBMP2(⁕).
Figure 11B:
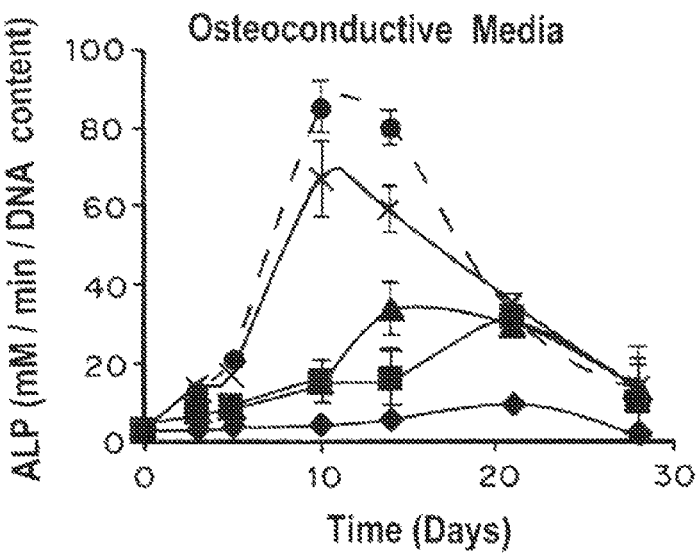
FIG. 11B is a line graph of ALP (mM/min/DNA content) versus time (days) of bone marrow-derived human mesenchymal stem cells in osteoconductive media.
Figure 11C:
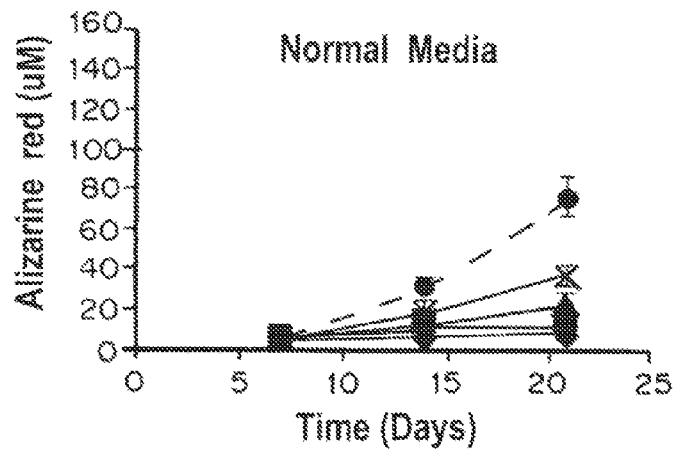
FIG. 11C is a line graph of Alizarine red (µM) versus time (days) of bone marrow-derived human mesenchymal stem cells in normal media.
Figure 11D:
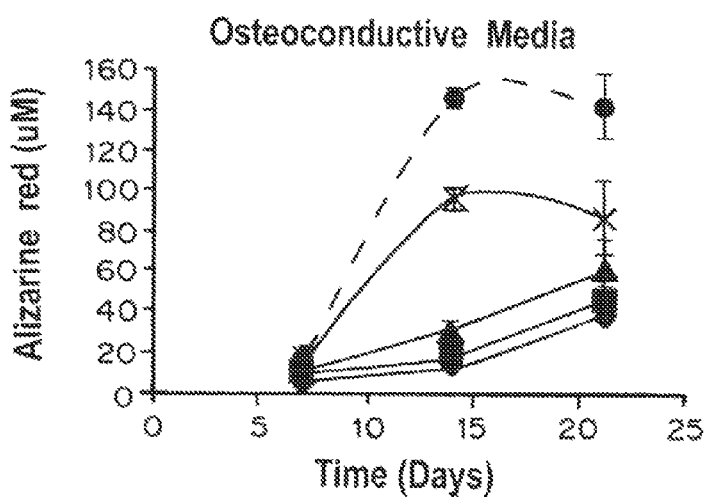
FIG. 11D is a line graph of Alizarine red (µM) versus time (days) of bone marrow-derived human mesenchymal stem cells in osteoconductive media.

The induction of ALP enzymatic activity in hMSCs was determined, over the basal levels, which indicated that after day 5 the ALP activity was significantly increased in hMScs treated with rhBMP2 loaded NPs in comparison to the cells treated with rhBMP2 added to the media on day 1 (positive control) (FIGS. 11A and 11B). The ALP activity peaked at day 10 and 14 in hMSCs treated with rhBMP2 loaded NPs and decreased thereafter at the onset of osteogenic differentiation and begin to induce mineralization, as observed by alizarine red assay. The ALP enzymatic activity at day 10 is 11- to 14-fold higher positive control in normal media and 13- to 17-fold higher in osteoconductive media (FIG. 11B). The ALP enzymatic activity attains the peak after day 14 in positive control cells as seen in FIG. 11A. The elevation in ALP enzymatic activity of hMSCs treated with rhBMP2 loaded NPs was re-confirmed by staining with ALP reagent and observing under optical microscope.

After day 14 the rhBMP2 loaded NPs induced mineralization in osteoconductive media as observed by alizarine red S assay. The extent of calcification induced by rhBMP2 loaded NPs was 8- to 12-fold higher in hMSCs as compared to positive control cells. The optical microscopy images of alizarine red shows node formation at day 21 in cells treated with rhBMP2 loaded NPs in osteoconductive media, whereas in control cells there is not much calcification.

The expression of osteogenic proteins such as osteocalcin and osteopointin were evaluated by immunostaining of hMSCs treated with rhBMP2 loaded NPs. The fluorescent microscopy images show relatively higher expression of these proteins in comparison to positive control cells.

This significant increase in the osteogenic differentiation of hMSCs and elevation in the early and late markers and calcification of hMSCs treated with rhBMP2 loaded NPs can be attributed to the sustained release of rhBMP2 from NPs in a bioactive form in comparison to cells treated with same amount of rhBMP2 of day one. It has been previously studied that the low half-life of proteins like rhBMP2 makes it necessary to continuously replenish the molecule at the target site for the effective function, and thus many fold higher protein need to be given in order to maintain the therapeutic dose of the molecule. This leads to significant side effects of proteins like growth factors, cytokines and interleukins. NPs play their role in maintaining the effective protein concentration in the site of action over a much longer period of time. Thus creating effective delivery solutions for cytokines and growth factors such as BMP2 with minimal side effects and minimal dose is needed.

The data suggests that NPs with encapsulated CaP and rhBMP-2 enhance the ALP activity and could initiate osteogenesis. The effect of PEG-PLGA and PEG-PLGA/CaP NPs, with and without rhBMP-2, on mineralized extracellular matrix (ECM) production was investigated. Mineralized matrix was stained with Alizarin Red on day 7, 14 and 21. At day 14 onwards, clusters of mineralized matrix were noticed in the normal media and osteoconductive media. In the presence of PEG-PLGA/rhBMP-2 and PEG-PLGA/CaP-rhBMP-2 NPs larger mineralized deposit formation is triggered, in osteoconductive media. At day 21, small mineralized deposits could be observed in normal media in the presence of PEG-PLGA/CaP-rhBMP-2, indicating that the nanoparticles induce the reorganization and remodeling of the ECM towards osteogenesis. On the other hand, in osteoconductive media, the presence of PEG-PLGA/rh-BMP-2 and PEG-PLGA/CaP-rhBMP-2 caused an enhanced calcification response, reaching a uniform distribution of the mineralized matrix.

Example 8: In-vivo Biodistribution Studies

Materials and Methods

Athymic nude mice and Balb/c at 6 weeks were purchased from Charles River for biodistribution studies. AF647 labeled alendronate conjugated, rhBMP2 encapsulated NPs were synthesized using nanoprecipitation as the method of formulation, with 5% of the total polymer as PLGA-AF647 and characterized for stability prior to injection. Mice were fed Non-Fluorescent Diet 48 hours prior to injection and kept on the diet for the remainder of the study. For whole mouse imaging, 1 mg of AF647 labeled NPs in PBS was injected i.v. for IVIS FLIT imaging (Caliper Life Sciences) in the Koch Institute Whole Animal Imaging Core and time-points examined were 1 and 24 hours. Each mouse had >30 point source selections, ex: 675 nm, em: 720 nm. For organ distribution studies, 300 μg of AF647 labeled NPs were injected i.v. and organs were subsequently removed after removal of whole blood through cardiac puncture at timepoints of 1 hr and 24 hr. All quantitative imaging analysis was conducted using Living Image 4.2 software. All statistics were taken using Prism 5.0 Student's unpaired t-test.

Statistical Analysis

Data are presented as mean±standard deviation of the mean values. Statistical analysis was performed using GraphPad Prism 5.00 software (San Diego, USA) to determine the statistical differences. Statistical differences ($*p<0.001, p<0.01, *p<0.05$) were determined using one-way analysis of variance (ANOVA) for an average of three to six replicates followed by post hoc Tukey's method to test all pair-wise mean comparisons.

Results

Figure 12:
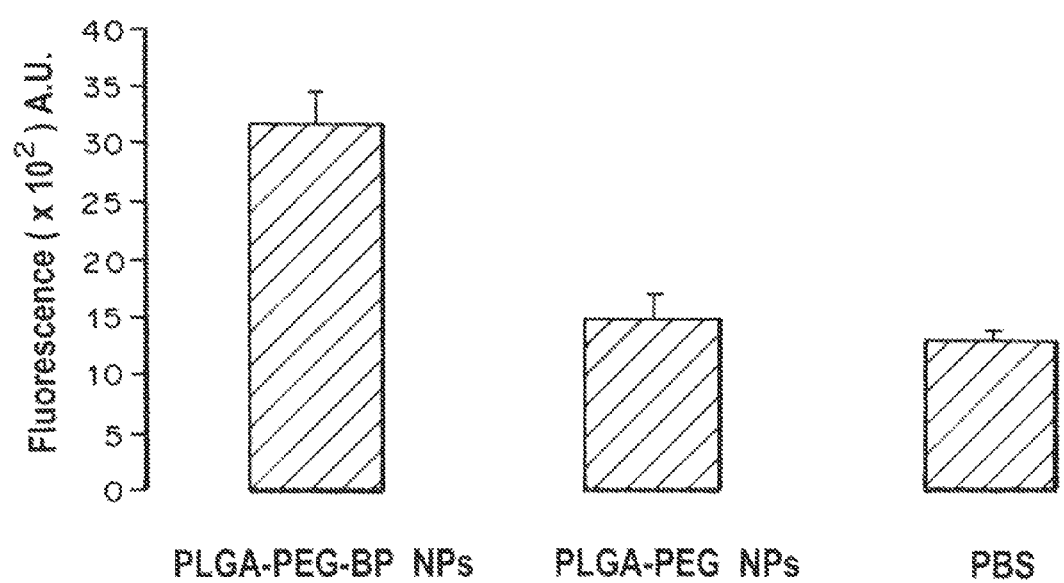
FIG. 12 is a bar graph of fluorescence ($\times 10^3$) A.U. in femur and spine of mice injected with fluorescent NPs (labeled with PLGA-Alexa647), as quantified from histology of dissected bones, 24 hrs after the injection. The nanoparticles used were PLGA-b-PEG-BP (left) and PLGA-PEG (middle), using phosphate buffered saline (PBS) as a control (right).

To determine whether the engineered, alendronate conjugated PLGA-PEG NPs are able to target bone to deliver a desired payload, fluorescent bio-distribution studies were conducted using IVIS. FIG. 12 shows NPs labeled with PLGA-Alexa647 in femur and spine quantified from histology. Animals injected with non-targeted and targeted nanoparticles could not be differentiated from each other at 1 hour. Notably at 24 hours, mice injected with targeted nanoparticles show increased retaining nanoparticles. Upon further investigation with bone histology, it was observed that although there were increased levels of NP accumulation at 24 hours for targeted nanoparticles in bone (femur and spine). Thus the targeted nanoparticles showed significance in binding compared to non-targeted nanoparticles at 24 hours. In summary, the in vivo biodistribution study compliments the in vitro and ex vivo data to highlight the potential in utilizing alendronate conjugated nanoparticles in drug delivery for targeting bone.

We claim:

1. Polymeric nanoparticles comprising a blend of
   (a) amphiphilic polymers comprising hydrophobic ends and hydrophilic ends, the hydrophilic ends of the amphiphilic polymers having bound thereto a targeting element specifically binding to bone, mineral, or metal ions, and
   (b) hydrophobic or amphiphilic polymer not having a targeting element bound thereto,
   the nanoparticles being formed by self-assembly of the blend, wherein the hydrophobic ends of the amphiphilic polymers are predominantly oriented toward the nanoparticle core, and the targeting elements are predominantly on the surface of the nanoparticle, and
   one or more therapeutic, prophylactic or diagnostic agents encapsulated therein,
   wherein the amphiphilic polymer having the targeting element bound thereto is in a percentage relative to the hydrophobic or amphiphilic polymer not having targeting element bound thereto of between 10 and 30% weight/weight.

2. The nanoparticles of claim 1, wherein the targeting element of the targeting element-polymer-conjugate comprises a phosphonate.

3. The nanoparticles of claim 2, wherein the phosphonate is a bisphosphonate.

4. The nanoparticles of claim 3, wherein the bisphosphonate is selected from the group consisting of alendronate, etidronate, clodronate, tiludronate, pamidronate, neridronate, olpadronate, ibandronate, risedronate, zoledronate, or combinations thereof.

5. The nanoparticles of claim 1, wherein the amphiphilic polymer having bound thereto the targeting element or the amphiphilic polymer not having the targeting element bound thereto comprises poly(lactide-co-glycolide)-b-poly(ethylene glycol) (PLGA-b-PEG).

6. The nanoparticles of claim 1, dispersed in a coating on a medical device or implant.

7. The nanoparticles of claim 2, comprising a chemotherapeutic agent.

8. The nanoparticles of claim 1, comprising a bone morphogenic protein.

9. The nanoparticles of claim 1, comprising PLGA-b-PEG-bisphosphonate that forms an outer PEG-bisphosphonate surface; and a PLGA hydrophobic core.

10. The nanoparticles of claim 1, in a bone cement or adhesive.

11. The nanoparticles of claim 1, comprising therapeutic agents released over time.

12. The nanoparticles of claim 1 formed by self-assembly that orients the amphiphilic polymers with the hydrophilic end to the surface and the hydrophobic ends to the core.

13. The nanoparticles of claim 1 dispersed in a solution for administration by coating or dipping onto or into an implant during implantation or surgery.

14. A pharmaceutical composition comprising the nanoparticles of claim 1.

15. A method for treating a bone disorder in a subject in need thereof; comprising the steps of
administering to the subject the nanoparticles of claim 1 in an amount effective to treat one or more symptoms of the bone disorder.

16. A method of improving osseointegration of a medical device into a bone of a subject comprising coating the device with the nanoparticles of claim 1 and implanting the device into the bone of the subject, wherein the nanoparticle-coated device shows improved osseointegration relative to an uncoated medical device.

17. A method of treating bone cancer in a subject in need thereof, comprising administering the nanoparticles of claim 1 in an amount effective to treat one or more symptoms of bone cancer, wherein the nanoparticle is loaded with one or more chemotherapeutic agent.

18. A method for the targeted delivery of a therapeutic agent comprising loading the therapeutic agent into the nanoparticles of claim 1 and administering the loaded nanoparticle to a bone or mineralized area of a subject in need thereof.

19. The nanoparticles of claim 4, wherein the bisphosphonate is alendronate.

20. The nanoparticles of claim 1 wherein the ratio of the targeting element-polymer conjugate to the polymer not having targeting element conjugated thereto is 1:4 by weight/weight for bone targeting.

21. The nanoparticles of claim 4 wherein the percentage of the targeting element-polymer conjugate to total polymer is 20% weight/weight and has an improved half-life in the blood of a subject.

* * * * *